(12) United States Patent
Saito

(10) Patent No.: US 12,020,420 B2
(45) Date of Patent: Jun. 25, 2024

(54) ENDOSCOPE SYSTEM, METHOD FOR ACTIVATING ENDOSCOPE SYSTEM, AND IMAGE PROCESSING APPARATUS

(71) Applicant: FUJIFILM Corporation, Tokyo (JP)

(72) Inventor: Takaaki Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 396 days.

(21) Appl. No.: 17/455,094

(22) Filed: Nov. 16, 2021

(65) Prior Publication Data
US 2022/0076400 A1 Mar. 10, 2022

Related U.S. Application Data

(63) Continuation of application No. PCT/JP2020/019512, filed on May 15, 2020.

(30) Foreign Application Priority Data

May 21, 2019 (JP) ................. 2019-095093

(51) Int. Cl.
*G06T 7/11* (2017.01)
*A61B 1/00* (2006.01)
(Continued)

(52) U.S. Cl.
CPC ............ *G06T 7/001* (2013.01); *A61B 1/0005* (2013.01); *A61B 5/14551* (2013.01);
(Continued)

(58) Field of Classification Search
CPC ......... G06T 7/0012; G06T 7/001; G06T 7/90; A61B 5/14551; A61B 5/4331; A61B 5/145; A61B 5/0075
See application file for complete search history.

(56) References Cited

U.S. PATENT DOCUMENTS

2012/0157775 A1 6/2012 Yamaguchi
2013/0113906 A1 5/2013 Saito
(Continued)

FOREIGN PATENT DOCUMENTS

JP 2012-130429 A 7/2012
JP 2013-099464 A 5/2013
(Continued)

OTHER PUBLICATIONS

International Search Report issued in PCT/JP2020/019512; dated Jul. 14, 2020.
(Continued)

*Primary Examiner* — Phuoc H Doan
(74) *Attorney, Agent, or Firm* — Studebaker & Brackett PC

(57) ABSTRACT

An actual measurement value calculation unit calculates a first actual measurement value of oxygen saturation of a tissue to be observed. A reference value calculation unit calculates a first reference value of the oxygen saturation of the tissue to be observed. A relative value calculation unit calculates a relative value of the first actual measurement value with reference to the first reference value. An image generation unit generates an image of the relative value of the first actual measurement value on the basis of an evaluation color table to generate an evaluation oxygen-saturation image. A display unit displays the evaluation oxygen-saturation image.

14 Claims, 19 Drawing Sheets

(51) Int. Cl.
    *A61B 5/1455*    (2006.01)
    *A61B 5/1459*    (2006.01)
    *G06T 7/00*    (2017.01)
    *G06T 7/90*    (2017.01)

(52) U.S. Cl.
    CPC .............. *A61B 5/1459* (2013.01); *G06T 7/90* (2017.01); *G06T 2207/10024* (2013.01); *G06T 2207/10068* (2013.01); *G06T 2207/20224* (2013.01); *G06T 2207/30104* (2013.01)

(56) References Cited

U.S. PATENT DOCUMENTS

| | | |
|---|---|---|
| 2015/0208958 A1 | 7/2015 | Kaku |
| 2016/0287061 A1 | 10/2016 | Shigeta |
| 2019/0069768 A1* | 3/2019 | Chiba .............. A61B 1/000094 |
| 2019/0223703 A1* | 7/2019 | Fukuda ................ A61B 1/0638 |

FOREIGN PATENT DOCUMENTS

| | | |
|---|---|---|
| JP | 2014-076375 A | 5/2014 |
| JP | 2015-139657 A | 8/2015 |
| JP | 2016-192985 A | 11/2016 |

OTHER PUBLICATIONS

Written Opinion of the International Searching Authority issued in PCT/JP2020/019512; dated Jul. 14, 2020.

The extended European search report issued by the European Patent Office dated Jun. 3, 2022, which corresponds to European Patent Application No. 20809750.1-1126 and is related to U.S. Appl. No. 17/455,094.

* cited by examiner

| ILLUMINATION LIGHT | IMAGING (IMAGE SIGNAL) |
|---|---|
| FIRST BLUE LIGHT BS<br>GREEN LIGHT G<br>RED LIGHT R | (Bc, Gc, Rc) |

FIG. 8

| | PHOTOGRAPHIC SUBJECT | ILLUMINATION LIGHT | | IMAGING (IMAGE SIGNAL) | |
|---|---|---|---|---|---|
| ISCHEMIA EVALUATION MODE OR OXYGEN SATURATION MODE | FIRST OBSERVATION TARGET | FIRST LIGHT EMISSION | | FIRST IMAGING | FIRST SPECTRAL IMAGES |
| | | | FIRST BLUE LIGHT BS GREEN LIGHT G RED LIGHT R | (B1m, G1m, R1m) | |
| | | SECOND LIGHT EMISSION | | SECOND IMAGING | |
| | | | SECOND BLUE LIGHT BL GREEN LIGHT G RED LIGHT R | (B2m, G2m, R2m) | |

FIG. 9

| | PHOTOGRAPHIC SUBJECT | ILLUMINATION LIGHT | | IMAGING (IMAGE SIGNAL) | |
|---|---|---|---|---|---|
| REFERENCE-VALUE CALCULATION MODE | SECOND OBSERVATION TARGET OR THIRD OBSERVATION TARGET | FIRST LIGHT EMISSION | | FIRST IMAGING | SECOND SPECTRAL IMAGES OR THIRD SPECTRAL IMAGES |
| | | | FIRST BLUE LIGHT BS GREEN LIGHT G RED LIGHT R | (B1n, G1n, R1n) | |
| | | SECOND LIGHT EMISSION | | SECOND IMAGING | |
| | | | SECOND BLUE LIGHT BL GREEN LIGHT G RED LIGHT R | (B2n, G2n, R2n) | |

FIG. 28
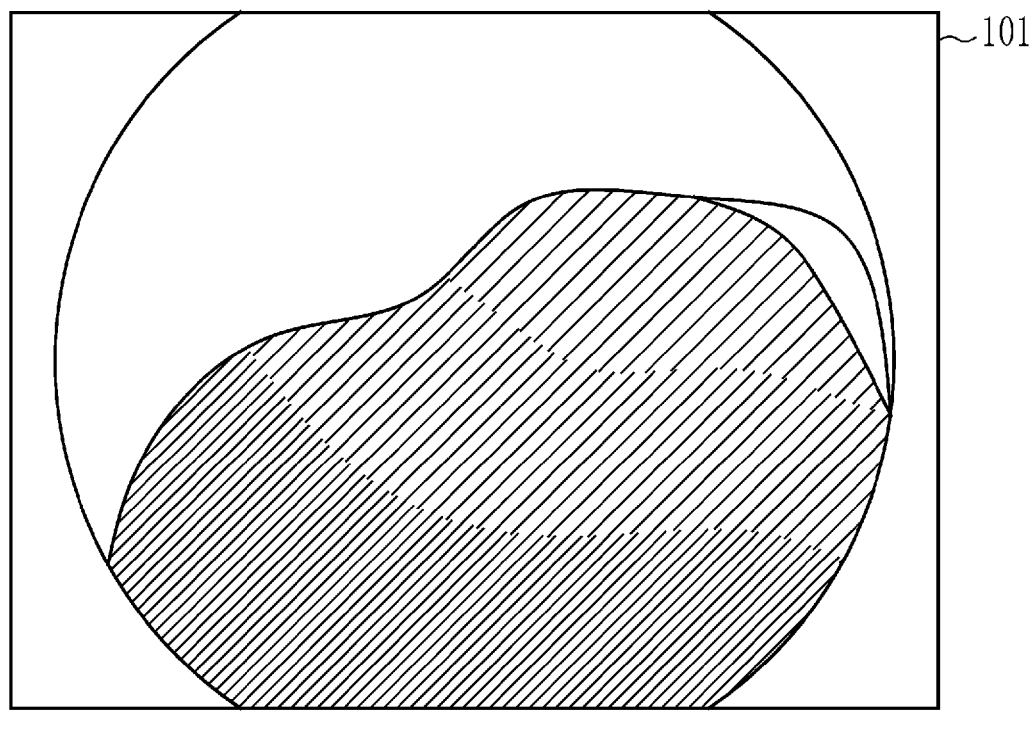
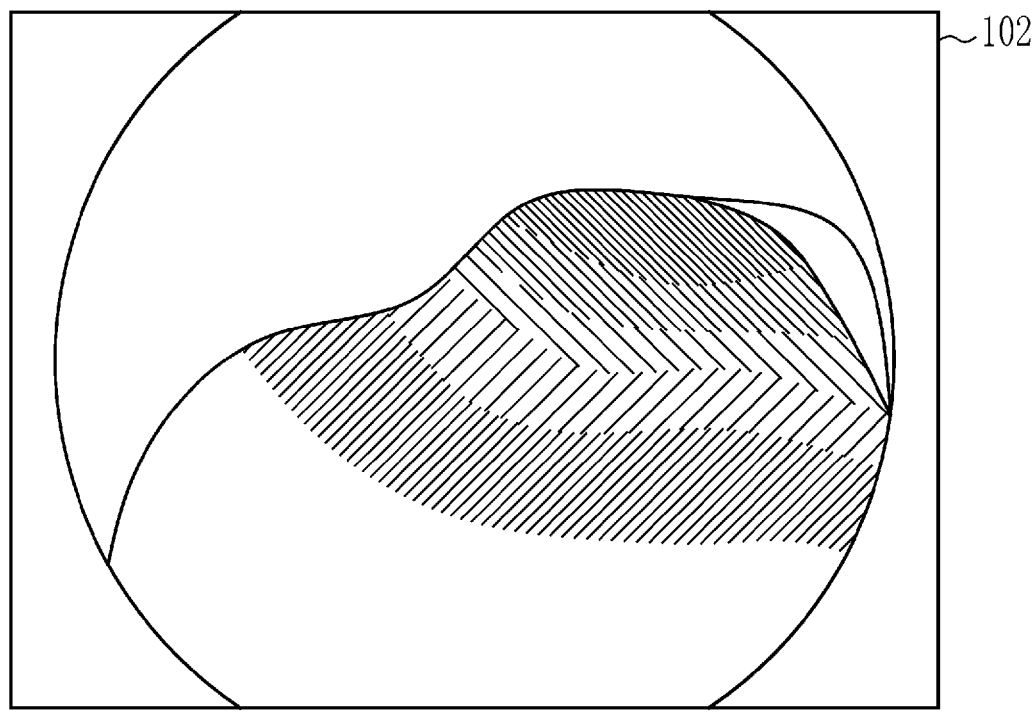

ENDOSCOPE SYSTEM, METHOD FOR ACTIVATING ENDOSCOPE SYSTEM, AND IMAGE PROCESSING APPARATUS

CROSS-REFERENCE TO RELATED APPLICATIONS

This application is a Continuation of PCT International Application No. PCT/JP2020/019512 filed on 15 May 2020, which claims priority under 35 U.S.C § 119(a) to Japanese Patent Application No. 2019-095093 filed on 21 May 2019. The above application is hereby expressly incorporated by reference, in its entirety, into the present application.

BACKGROUND OF THE INVENTION

1. Field of the Invention

The present invention relates to an endoscope system, a method for activating the endoscope system, and an image processing apparatus, which are used as treatment during or after surgery in excision of a tumor portion such as a cancer.

2. Description of the Related Art

In recent years, laparoscopic surgery has attracted attention in which surgery is performed using a laparoscope. For example, in the case of surgical colorectal cancer resection using a laparoscope, the laparoscope and a surgical treatment tool are inserted into the abdominal cavity of a patient through a trocar inserted into the abdomen of the patient. Then, the abdominal cavity is inflated with a pneumoperitoneum gas composed of carbon dioxide, and an image of the inside of the abdominal cavity is displayed on a monitor. Then, while observing the image of the inside of the abdominal cavity displayed on the monitor, the operator excises a portion affected by a primary lesion in the large intestine. The sectioned parts of the large intestine resulting from excision of the primary lesion are sutured together with an automatic suturing device or the like.

After surgery, in the process of normal wound agglutination after suturing, activation of fibroblasts in tissue usually occurs two to three days after suturing, and agglutination is completed in around seven days. However, if the agglutination is inhibited by several factors during agglutination of tissues, insufficient agglutination of tissues may occur, resulting in suture failure in which part or the whole of the suture site is dissociated.

In a surgical operation such as intestinal anastomosis after colorectal cancer resection, it is important to connect intestinal tracts at a portion where blood flows as much as possible to prevent suture failure after the operation. The degree of blood flow is basically determined by visual inspection based on the color tone of the intestinal tracts. To visualize the ischemic boundary, which is difficult to observe through visual inspection, an angiographic method with administration of a fluorescent agent such as ICG (indocyanine green) is widely used. In the method based on ICG administration, it is necessary to wait several minutes after intravenous injection, and a dedicated light source and camera are required for observation of a fluorescence image. In addition, since the agent remains in the blood after being administered once, there is a problem such as difficulty in re-administration and re-observation. Accordingly, visualization or generation of images of the oxygen saturation of hemoglobin included in an observation target using an endoscope, that is, utilization of oxygen saturation imaging, is expected.

JP2014-76375A discloses an endoscope system including a setting changing means for changing reference information, which defines a correlation between oxygen saturation and pixel values obtained by capturing an image of an observation site, in accordance with the properties of the observation site in oxygen saturation imaging using an endoscope. As a result, highly reliable information on oxygen saturation can be acquired.

SUMMARY OF THE INVENTION

In a case where existing oxygen saturation imaging of an endoscope is utilized, for example, information on oxygen saturation for which an image is presented in pseudo-color can be used to obtain information on the levels of oxygen saturation. However, in the case of discrimination of an ischemic site using an image of oxygen saturation, the existing technique described above displays a normal portion and an ischemic portion in similar color tones, which may cause difficulty in discriminating the boundary between the normal site and the ischemic site.

It is an object of the present invention to provide an endoscope system, a method for activating the endoscope system, and an image processing apparatus, which enable display of a clearer index for determining the boundary between a normal site and an ischemic site, which can be a basis for judgment of an excision area, an anastomosis area, or any other area where suture failure is less likely to occur.

The present invention provides an endoscope system including a processor that calculates a first actual measurement value of oxygen saturation of a tissue to be observed on the basis of a plurality of first spectral images, calculates a first reference value of the oxygen saturation of the tissue to be observed on the basis of a plurality of second spectral images, calculates a relative value of the first actual measurement value with reference to the first reference value, and generates an image of the relative value of the first actual measurement value on the basis of an evaluation color table to generate an evaluation oxygen-saturation image; and a display that displays at least the evaluation oxygen-saturation image.

Preferably, the processor generates an image of the first actual measurement value on the basis of an observation color table to generate an observation oxygen-saturation image, and switches between an oxygen saturation mode for displaying at least the observation oxygen-saturation image on the display and an ischemia evaluation mode for displaying at least the evaluation oxygen-saturation image on the display.

Preferably, the processor sets, as the relative value of the first actual measurement value, a value obtained by subtracting the first reference value from the first actual measurement value.

Preferably, the processor generates the observation oxygen-saturation image on the basis of the observation color table in which a value in a range from 0% to 100% of the oxygen saturation and color information of the observation oxygen-saturation image are associated with each other in advance.

Preferably, the processor creates the evaluation color table in which the relative value of the first actual measurement value and color information of the evaluation oxygen-saturation image are associated with each other.

In the evaluation color table, preferably, the relative value of the first actual measurement value in a case where the relative value is 0 and a specific color in a warm color system of the evaluation oxygen-saturation image are associated with each other.

Preferably, the processor sets a lower limit value and/or an upper limit value of the relative value of the first actual measurement value associated with color information of the evaluation oxygen-saturation image to create the evaluation color table.

Preferably, the processor accepts an instruction to set the lower limit value and/or the upper limit value, and creates the evaluation color table using the lower limit value and/or the upper limit value based on the instruction.

Preferably, the processor calculates a second reference value of the oxygen saturation of the tissue to be observed on the basis of a plurality of third spectral images, calculates a relative value of the second reference value with reference to the first reference value, and sets the relative value of the second reference value as the lower limit value.

Preferably, the processor accepts an instruction to calculate the first reference value, and calculates the first reference value in accordance with the instruction.

Preferably, the processor calculates the first reference value or the second reference value by averaging second actual measurement values or third actual measurement values of the oxygen saturation, each of the second actual measurement values being calculated for a corresponding one of pixels of the plurality of second spectral images, each of the third actual measurement values being calculated for a corresponding one of pixels of the plurality of third spectral images.

Preferably, the processor determines a signal ratio having dependence on both the oxygen saturation and blood volume on the basis of the plurality of first spectral images, the plurality of second spectral images, or a plurality of third spectral images, stores a correlation between the oxygen saturation and the signal ratio, and calculates the first actual measurement value, a second actual measurement value, or a third actual measurement value of the oxygen saturation corresponding to the signal ratio on the basis of the correlation.

Preferably, the first spectral images are images obtained by capturing an image of a first observation target that includes a lesion, and the second spectral images or the third spectral images are images obtained by capturing an image of a second observation target or a third observation target that does not include the lesion.

Further, the present invention provides a method for activating an endoscope system, including an actual measurement value calculation step of calculating a first actual measurement value of oxygen saturation of a tissue to be observed on the basis of a plurality of first spectral images; a reference value calculation step of calculating a first reference value of the oxygen saturation of the tissue to be observed on the basis of a plurality of second spectral images; a relative value calculation step of calculating a relative value of the first actual measurement value with reference to the first reference value; an image generation step of generating an image of the relative value of the first actual measurement value on the basis of an evaluation color table to generate an evaluation oxygen-saturation image; and a display step of displaying the evaluation oxygen-saturation image.

Further, the present invention provides an image processing apparatus that an endoscope system includes. The image processing apparatus calculates a first actual measurement value of oxygen saturation of a tissue to be observed on the basis of a plurality of first spectral images; calculates a first reference value of the oxygen saturation of the tissue to be observed on the basis of a plurality of second spectral images; calculates a relative value of the first actual measurement value with reference to the first reference value; and generates an image of the relative value of the first actual measurement value on the basis of an evaluation color table to generate an evaluation oxygen-saturation image.

According to the present invention, it is possible to display a clearer index for determining the boundary between a normal site and an ischemic site, which can be a basis for judgment of an excision area, an anastomosis area, or any other area where suture failure is less likely to occur.

BRIEF DESCRIPTION OF THE DRAWINGS

FIG. 8 is an explanatory diagram of a light emission pattern and the like in an ischemia evaluation mode or an oxygen saturation mode;
FIG. 9 is an explanatory diagram of a light emission pattern and the like in a reference-value calculation mode.

FIG. 28 is an explanatory diagram of a case where the observation image and the evaluation image are compared, switched, and displayed.

DESCRIPTION OF THE PREFERRED EMBODIMENTS

Figure 1:
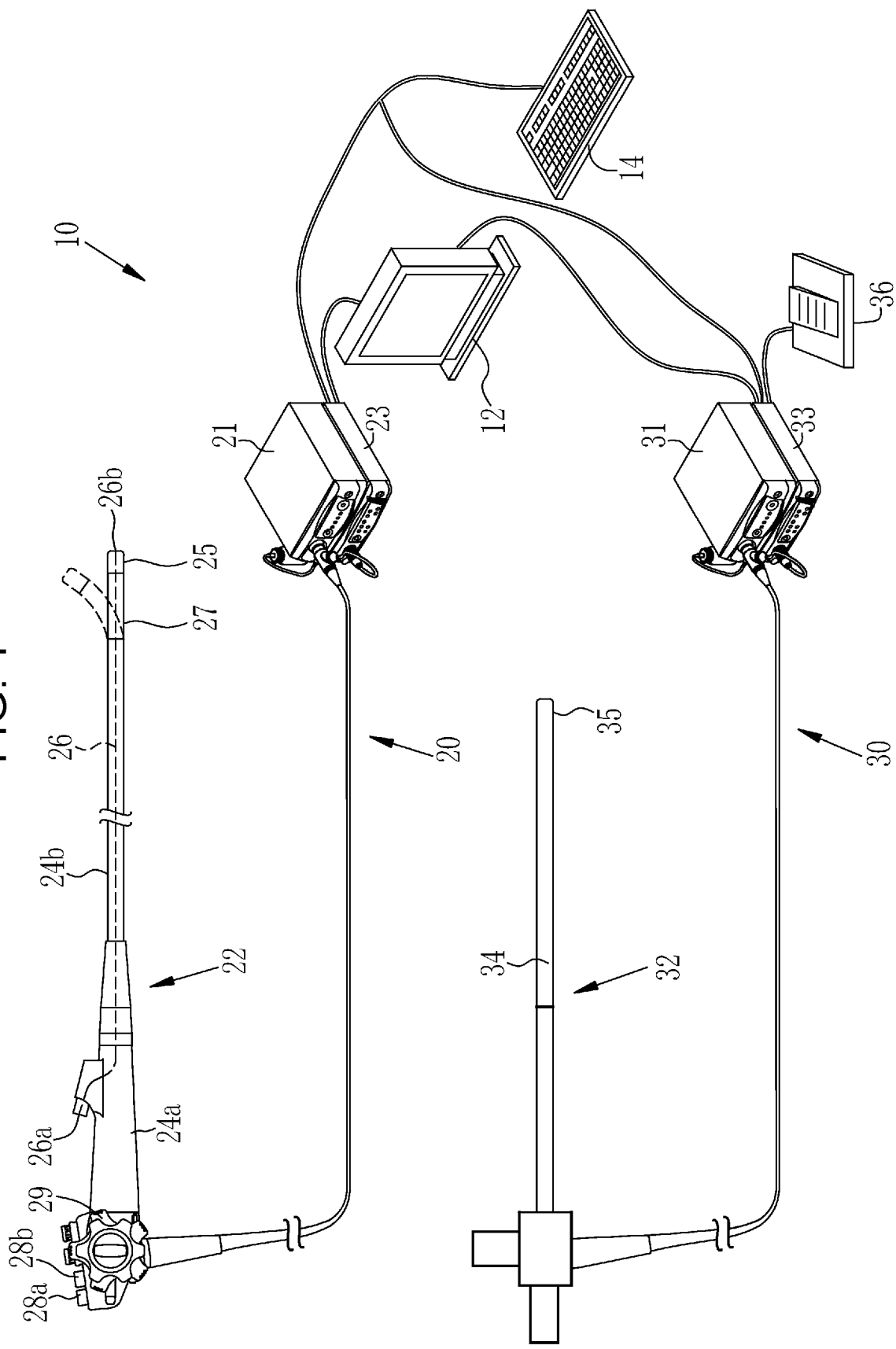
FIG. 1 is an external view of an endoscope system.

As illustrated in FIG. 1, in this embodiment, an endoscope system 10 is constituted by a lumen endoscope system 20 and an abdominal-cavity endoscope system 30 and is used to excise a tumor portion generated in the large intestine. The endoscope system 10 includes at least one of the lumen endoscope system 20 or the abdominal-cavity endoscope system 30. Before excision of the tumor portion, first, the lumen endoscope system 20 is used to detect the tumor portion in the large intestine and place a mark on a certain range (excision range) including the tumor portion. Then, the abdominal-cavity endoscope system 30 is used to excise the excision range on which the mark is placed in the large intestine and suture the large intestine, which is sectioned by the excision of the tumor portion. Finally, the lumen endoscope system 20 is used to check whether the sutured sections have been agglutinated in an organized manner.

The lumen endoscope system 20 includes a lumen light source device 21 that generates light for illuminating the inside of a lumen, a lumen endoscope apparatus 22 that irradiates the inside of the lumen with light from the lumen light source device 21 and captures a reflected image thereof, and a lumen processor apparatus (lumen image processing apparatus) 23 that performs image processing on an image signal obtained from the image captured by the lumen endoscope apparatus 22. The lumen processor apparatus 23 is connected to a display device 12 (display unit) that displays an endoscopic image or the like obtained by the image processing and an input device 14 constituted by a keyboard or the like. The display device 12 is, for example, a display.

The lumen endoscope apparatus 22 captures an image of an observation target to obtain an image. The lumen endoscope apparatus 22 is a soft endoscope and includes a lumen endoscope operation portion 24a, a flexible lumen endoscope insertion portion 24b, and a scope distal end portion 25 disposed at the distal end of the flexible lumen endoscope insertion portion 24b and configured to emit light toward the inside of a lumen and capture a reflected image of the inside of the lumen. The lumen endoscope apparatus 22 has a bending portion 27 disposed on the distal end side of the lumen endoscope insertion portion 24b. The lumen endoscope operation portion 24a has an angle knob 29 to be used for an operation for bending the bending portion 27. The bending portion 27 bends in response to an operation of the angle knob 29 to direct the scope distal end portion 25 to the desired direction. The scope distal end portion 25 is provided with an ejection port (not illustrated) from which a washing liquid is ejected toward the observation target.

The lumen endoscope operation portion 24a is further provided with, in addition to the angle knob 29, a mode switch 28a to be used for switching the observation mode, and a reference value calculation instruction portion 28b that accepts an instruction to calculate a reference value.

The lumen endoscope apparatus 22 is provided with a forceps channel 26 for inserting a treatment tool such as a hemostatic probe. The treatment tool is inserted into the forceps channel 26 from a forceps inlet 26a disposed in the lumen endoscope operation portion 24a, and the treatment tool inserted into the forceps channel 26 protrudes from a forceps outlet 26b of the scope distal end portion 25.

Figure 2:
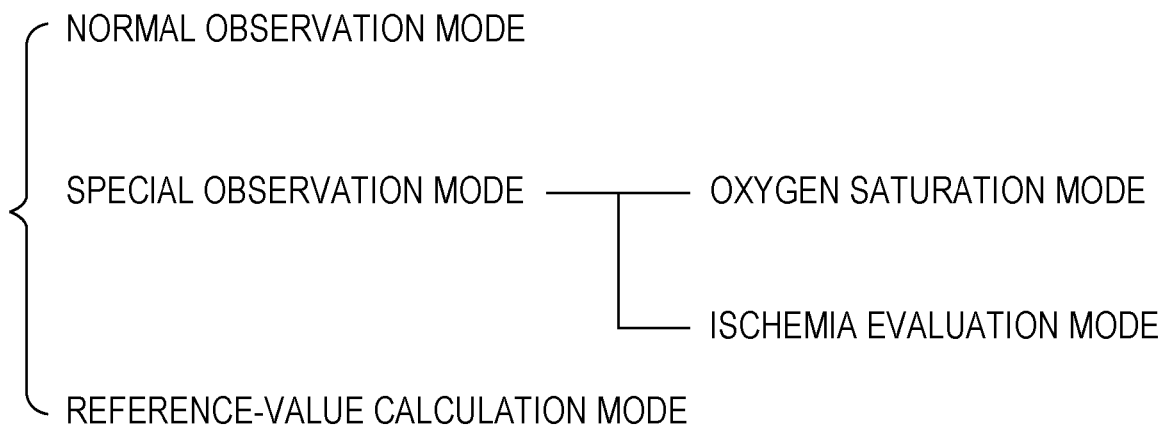
FIG. 2 is an explanatory diagram of observation modes.

As illustrated in FIG. 2, the lumen endoscope system 20 includes, as observation modes, at least two modes, that is, a normal observation mode and a special observation mode. In the normal observation mode, an image with natural tones of color (hereinafter referred to as a normal image), which is obtained by capturing an image of a part to be observed using white light as illumination light, is displayed on a monitor. In the special observation mode, an image of the oxygen saturation of the tissue to be observed is generated and displayed on the monitor.

The special observation mode includes at least two types of modes. One is an oxygen saturation mode, and the other is an ischemia evaluation mode. In the oxygen saturation mode, an image of the oxygen saturation of the tissue to be observed ($StO_2$ (tissue oxygen saturation)) is generated to obtain an observation oxygen-saturation image, and the observation oxygen-saturation image is displayed on the monitor. In the ischemia evaluation mode, the relative value of the oxygen saturation of the tissue to be observed is calculated, an image of the relative value is generated to obtain an evaluation oxygen-saturation image, and the evaluation oxygen-saturation image is displayed on the monitor. Hereinafter, the observation oxygen-saturation image is referred to as an observation image, and the evaluation oxygen-saturation image is referred to as an evaluation image.

Switching between the normal observation mode and the special observation mode and switching between the oxygen saturation mode and the ischemia evaluation mode are performed in accordance with, for example, an instruction from the mode switch 28a of the lumen endoscope apparatus 22 or the like. The mode switch 28a is a scope button. Each time the scope button of the mode switch 28a is pressed, the observation mode may be cyclically switched in the order of the normal observation mode, the oxygen saturation mode of the special observation mode, the ischemia evaluation mode of the special observation mode, and the normal observation mode.

The abdominal-cavity endoscope system 30 includes an abdominal-cavity light source device 31 that generates light for illuminating the inside of the abdominal cavity, an abdominal-cavity endoscope apparatus 32 that irradiates the inside of the abdominal cavity with light from the abdominal-cavity light source device 31 and captures a reflected image thereof, and an abdominal-cavity processor apparatus (abdominal-cavity image processing apparatus) 33 that performs image processing on an image signal obtained from the image captured by the abdominal-cavity endoscope apparatus 32. The abdominal-cavity processor apparatus 33 is connected to the display device 12 and the input device 14. The abdominal-cavity endoscope apparatus 32 captures an image of the observation target to obtain an image. The abdominal-cavity endoscope apparatus 32 is a hard endoscope and includes a hard abdominal-cavity endoscope insertion portion 34 and an abdominal-cavity endoscope distal end portion 35 disposed at the distal end of the abdominal-cavity endoscope insertion portion 34 and configured to emit light toward the inside of the abdominal cavity and capture a reflected image of the inside of the abdominal cavity.

Like the lumen endoscope system 20, the abdominal-cavity endoscope system 30 includes, as observation modes, at least two modes, that is, a normal observation mode and a special observation mode. The special observation mode includes at least two types of modes, one being an oxygen saturation mode and the other being an ischemia evaluation mode. The oxygen saturation mode can be switched in accordance with an instruction from a foot switch 36 or the like connected to the abdominal-cavity processor apparatus 33.

The lumen endoscope system 20 and the abdominal-cavity endoscope system 30 may further include a reference-value calculation mode in addition to the modes described above. A reference value may be, for example, a reference value calculated in the reference-value calculation mode or a reference value set in advance. In the reference-value calculation mode, oxygen saturation included in the tissue to be observed is calculated and used as a reference value of the oxygen saturation. The reference-value calculation mode is switched in accordance with an instruction from, for example, the reference value calculation instruction portion 28b disposed in the lumen endoscope apparatus 22 or the like. The reference value calculation instruction portion 28b is a scope button. When the scope button of the reference value calculation instruction portion 28b is pressed, the mode is switched to the reference-value calculation mode, and the reference value is calculated. Thus, a reference value calculation instruction is issued when a region to be used as a reference is observed. After the reference value is calculated in the reference-value calculation mode, the mode automatically returns to the previous mode before the reference-value calculation mode.

Figure 3:
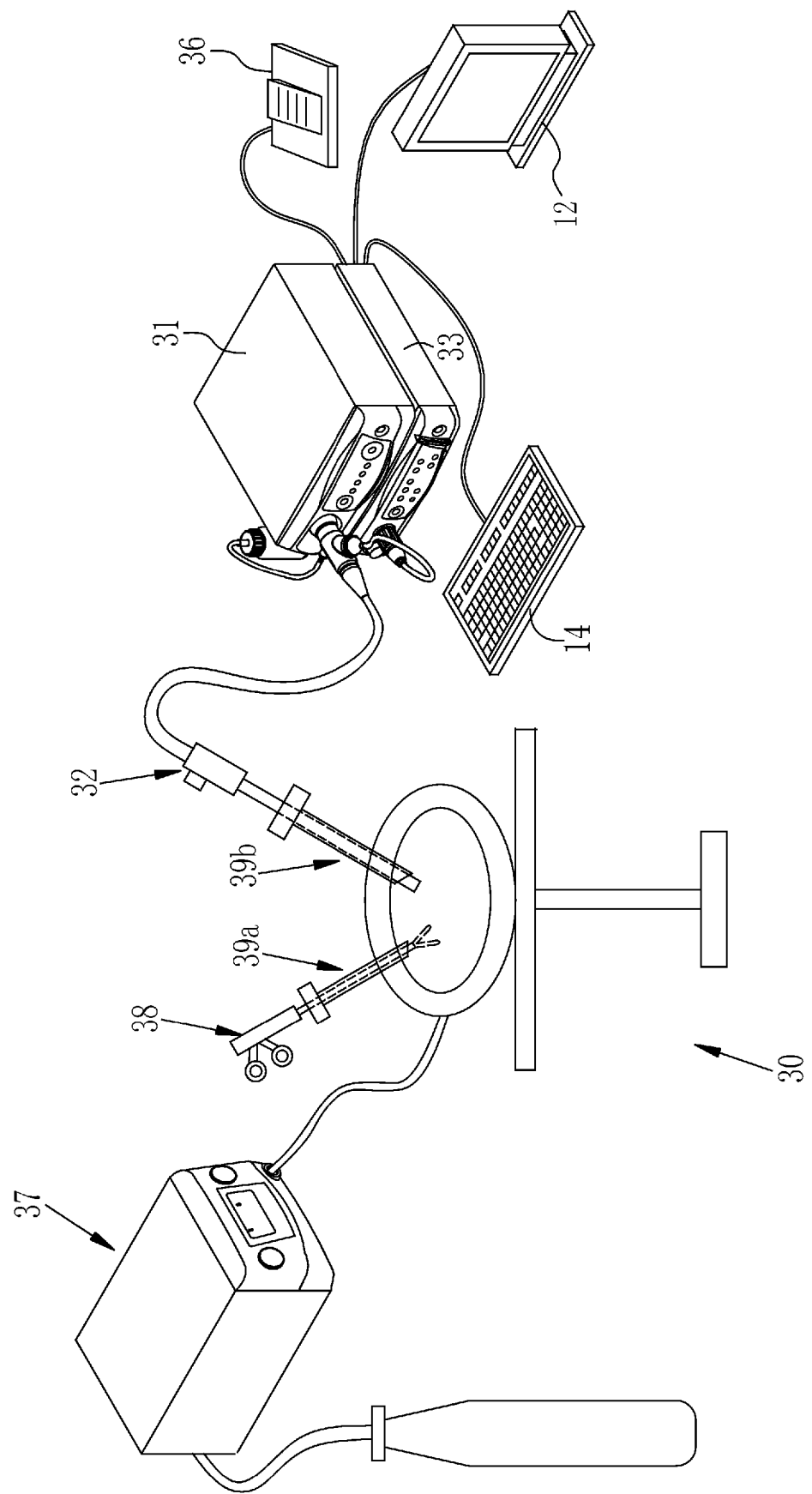
FIG. 3 is an external view of an abdominal-cavity endoscope system.

As illustrated in FIG. 3, in the abdominal-cavity endoscope system 30, a pneumoperitoneum device 37, a treatment tool 38, a trocar 39a, and a trocar 39b are used in addition to the abdominal-cavity light source device 31, the abdominal-cavity endoscope apparatus 32, and the abdominal-cavity processor apparatus 33 to observe the inside of the abdominal cavity and perform tumor-portion extraction surgery. In the abdominal-cavity endoscope system 30, first, $CO_2$ (carbon dioxide) gas is supplied from the pneumoperitoneum device 37 to the inside of the abdominal cavity to insufflate the abdominal cavity. This ensures a visual field and a surgical field in the abdominal cavity.

Then, the treatment tool 38 is inserted into the abdominal cavity through the trocar 39a, and the abdominal-cavity endoscope apparatus 32 is inserted into the abdominal cavity through the trocar 39b. The trocar 39a and the trocar 39b each include a metal hollow tube and an operator gripping portion. The operator inserts the sharp distal ends of the hollow tubes into the abdominal region while gripping the operator gripping portions to insert the hollow tubes into the abdominal cavity. The treatment tool 38 and the abdominal-cavity endoscope apparatus 32 are inserted with the trocar 39a and the trocar 39b whose hollow tubes are inserted into the abdominal cavity in the way described above, respectively.

Figure 4:
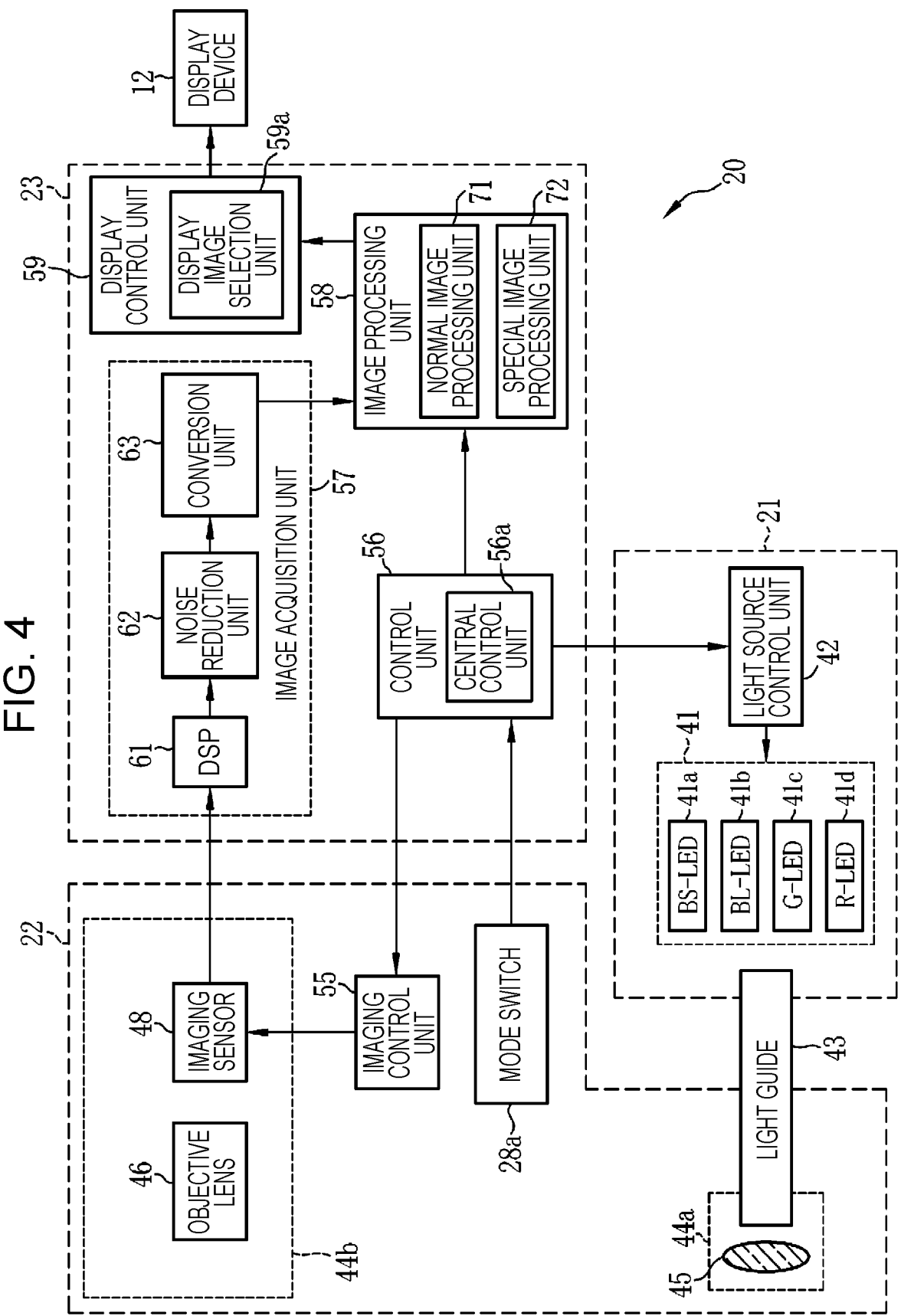
FIG. 4 is a block diagram of a lumen endoscope system.

While the lumen endoscope system 20 will hereinafter be described as an example, the same applies to the abdominal-cavity endoscope system 30. As illustrated in FIG. 4, the lumen light source device 21 includes a light source 41 and a light source control unit 42. The light source 41 has, for example, a plurality of semiconductor light sources, each of which is turned on or off. When the light source 41 is turned on, illumination light for illuminating the observation target is emitted. In this embodiment, the light source 41 has LEDs of four colors, namely, a BS-LED (Blue Short-wavelength Light Emitting Diode) 41a, a BL-LED (Blue Long-wavelength Light Emitting Diode) 41b, a G-LED (Green Light Emitting Diode) 41c, and an R-LED (Red Light Emitting Diode) 41d.

The BS-LED 41a emits first blue light BS in the wavelength range of 450±10 nm. The BL-LED 41b emits second blue light BL in the wavelength range of 470±10 nm, which is longer than the first blue light BS. The G-LED 41c emits green light G over the wavelength range of 500 nm to 600 nm. The R-LED 41d emits red light R1n the wavelength range of 620±20 nm. The center wavelength and the peak wavelength of the light of each color may be the same or different.

The light source control unit 42 independently inputs control signals to the LEDs 41a to 41d to independently control turning on and off of the LEDs 41a to 41d, the amount of light emitted at the time of turning on, and the like. The control of turning on and off by the light source control unit 42 is different for each observation mode. In the case of the normal observation mode, the light source control unit 42 simultaneously turns on the BS-LED 41a, the G-LED 41c, and the R-LED 41d to simultaneously emit the first blue light BS, the green light G, and the red light R.

In the case of the special observation mode, the light source control unit 42 alternately performs first light emission for simultaneously turning on the BS-LED 41a, the G-LED 41c, and the R-LED 41d to simultaneously emit the first blue light BS, the green light G, and the red light R, and second light emission for simultaneously turning on the BL-LED 41b, the G-LED 41c, and the R-LED 41d to simultaneously emit the second blue light BL, the green light G, and the red light R.

The light emitted from each of the LEDs 41a to 41d is incident on a light guide 43. The light guide 43 is built in the lumen endoscope apparatus 22 and a universal cord. The universal cord is a cord that connects the lumen endoscope apparatus 22 to the lumen light source device 21 and the lumen processor apparatus 23. The light guide 43 propagates light to the scope distal end portion 25 of the lumen endoscope apparatus 22.

The lumen endoscope apparatus 22 is constituted by an electronic endoscope and includes an illumination optical system 44a that emits light guided by the light guide 43 toward the observation target, an imaging optical system 44b that captures an image of the observation target, and an imaging control unit 55. The lumen endoscope apparatus 22 further includes a connector portion (not illustrated) that connects the lumen endoscope apparatus 22 to the lumen light source device 21 and the lumen processor apparatus 23 in a removable manner.

The illumination optical system 44a and the imaging optical system 44b are disposed in the scope distal end portion 25 of the lumen endoscope apparatus 22. The illumination optical system 44a has an illumination lens 45. The observation target is irradiated with illumination light from the light guide 43 through the illumination lens 45. The imaging optical system 44b has an objective lens 46 and an imaging sensor 48. The objective lens 46 allows return light from the observation target illuminated with the illumination light to enter the imaging sensor 48. As a result, an image of the observation target is formed on the imaging sensor 48.

Figure 5:
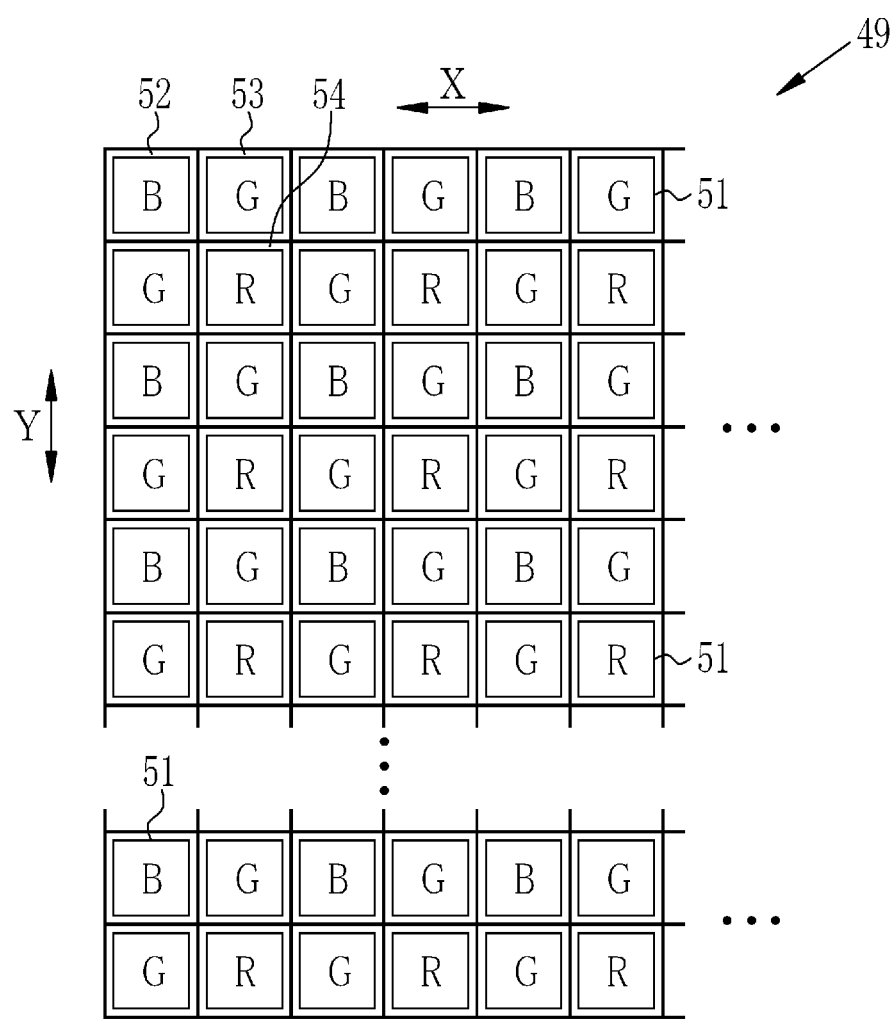
FIG. 5 is an explanatory diagram of pixels of an imaging sensor.

The imaging sensor 48 is a color imaging sensor that captures an image of the observation target illuminated with the illumination light and outputs an image signal. As illustrated in FIG. 5, the imaging sensor 48 has an imaging surface 49 on which a plurality of pixels 51 are two-dimensionally arranged in a matrix in a row direction (X direction) and a column direction (Y direction). Each of the pixels 51 is provided with any one of a B (blue) color filter 52, a G (green) color filter 53, and an R (red) color filter 54. The arrangement of the color filters 52 to 54 is a Bayer arrangement in which the G color filters 53 are arranged in panes at every other pixel and the B color filters 52 and the R color filters 54 are arranged on the remaining pixels in square grids.

Figures 6, 7:
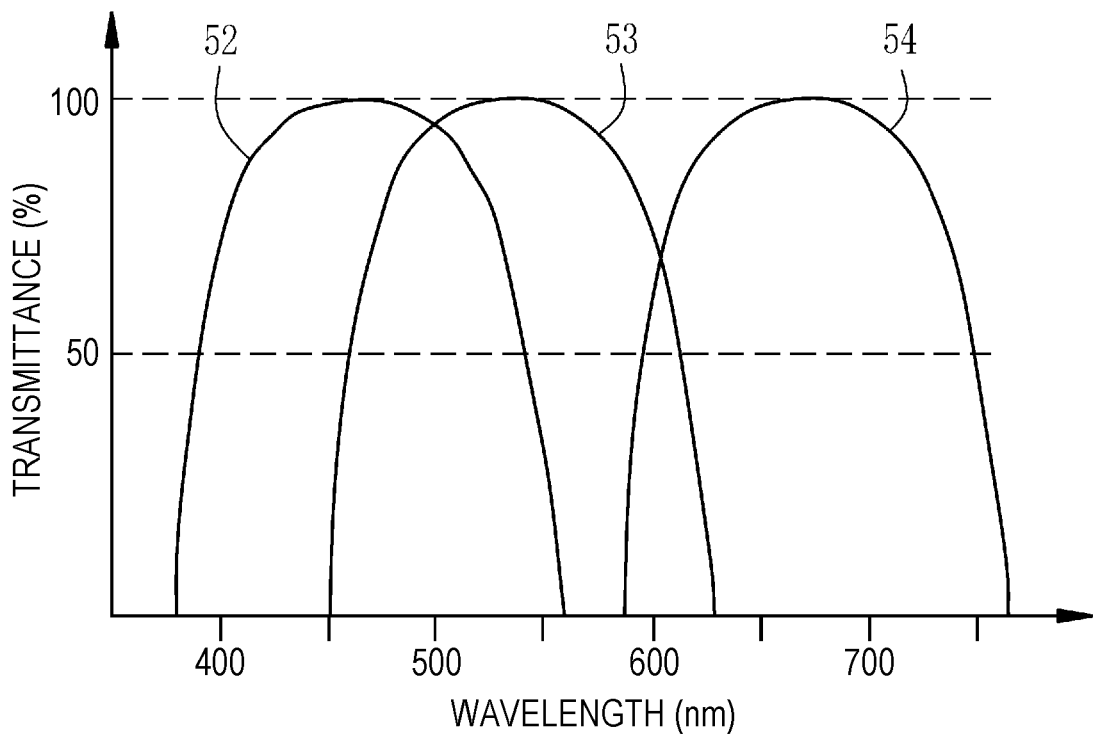
FIG. 6 is an explanatory diagram of color filters.
FIG. 7 is an explanatory diagram of a light emission pattern in a normal observation mode.

As illustrated in FIG. 6, the B color filters 52 each transmit light in the wavelength range of 380 nm to 560 nm. The G color filters 53 each transmit light in the wavelength range of 450 nm to 630 nm. The R color filters 54 each transmit light in the wavelength range of 580 nm to 760 nm. Thus, the B pixels have sensitivity to the wavelength range of 450±10 nm of the first blue light BS and the wavelength range of 470±10 nm of the second blue light BL. The G pixels have sensitivity to the wavelength range of 500 nm to 600 nm of the green light G. The R pixels have sensitivity to the wavelength range of 620±20 nm of the red light R.

A CCD (Charge Coupled Device) imaging sensor or a CMOS (Complementary Metal-Oxide Semiconductor) imaging sensor can be used as the imaging sensor 48 (see FIG. 4).

Instead of the primary color imaging sensor 48, a complementary color imaging sensor including complementary color filters of C (cyan), M (magenta), Y (yellow), and G (green) may be used. When the complementary color imaging sensor is used, image signals of four colors of C, M, Y, and G are output. The image signals of four colors of C, M, Y, and G are converted into image signals of three colors of R, G, and B through complementary color to primary color conversion. Thus, image signals of the respective colors of R, G, and B, which are similar to those for the imaging sensor 48, can be obtained.

The imaging sensor 48 receives light from the objective lens 46 on a light-receiving surface (imaging surface), photoelectrically converts the received light, and outputs an imaging signal (analog signal). Imaging control of the imaging sensor 48 is performed by the imaging control unit 55.

The imaging control unit 55 is electrically connected to the light source control unit 42 and performs imaging control in accordance with light emission control of the light source control unit 42. As illustrated in FIG. 7, in the case of the normal observation mode, the imaging control unit 55 controls the imaging sensor 48 to capture each frame of the observation target being illuminated with the first blue light BS, the green light G, and the red light R emitted under the control of the light source control unit 42. As a result, a Bc image signal is output from a B pixel, a Gc image signal is output from a G pixel, and an Rc image signal is output from an R pixel of the imaging sensor 48. The imaging control unit 55 synchronizes the exposure time of the imaging sensor 48 with the illumination time of the illumination light.

In the case of the oxygen saturation mode or the ischemia evaluation mode, the imaging control unit 55 performs different imaging controls for the first light emission and the second light emission. Specifically, in the case of the first light emission, as illustrated in FIG. 8, the imaging control unit 55 executes first imaging for capturing one frame of a first observation target being illuminated with the first blue light BS, the green light G, and the red light R, which are simultaneously emitted in the first light emission. As a result, during the first imaging, a B1m image signal is output from a B pixel, a G1m image signal is output from a G pixel, and an R1m image signal is output from an R pixel of the imaging sensor 48. The imaging control unit 55 further executes second imaging for capturing one frame of the first observation target being illuminated with the second blue light BL, the green light G, and the red light R, which are simultaneously emitted during the second light emission. As a result, during the second imaging, a B2m image signal is output from a B pixel, a G2m image signal is output from a G pixel, and an R2m image signal is output from an R pixel of the imaging sensor 48.

The B1m image signal, the G1m image signal, the R1m image signal, the B2m image signal, the G2m image signal, and the R2m image signal each correspond to a first spectral image of the present invention. Thus, a plurality of first spectral images include the B1m image signal, the G1m image signal, the R1m image signal, the B2m image signal, the G2m image signal, and the R2m image signal.

In the case of the reference-value calculation mode, the light source control unit 42 and the imaging control unit 55 function in a manner similar to that in the case of the oxygen saturation mode or the ischemia evaluation mode. In the reference-value calculation mode, thus, the light source control unit 42 alternately performs first light emission for simultaneously turning on the BS-LED 41a, the G-LED 41c, and the R-LED 41d to simultaneously emit the first blue light BS, the green light G, and the red light R, and second light emission for simultaneously turning on the BL-LED 41b, the G-LED 41c, and the R-LED 41d to simultaneously emit the second blue light BL, the green light G, and the red light R.

Further, in the reference-value calculation mode, the imaging control unit 55 performs different imaging controls for the first light emission and the second light emission. Specifically, in the case of the first light emission, as illustrated in FIG. 9, the imaging control unit 55 executes first imaging for capturing one frame of a second observation target or a third observation target being illuminated with the first blue light BS, the green light G, and the red light R, which are simultaneously emitted during the first light emission. A first reference value is calculated based on the second observation target, and a second reference value is calculated based on the third observation target. As a result, during the first imaging, a B1n image signal is output from a B pixel, a G1n image signal is output from a G pixel, and an R1n image signal is output from an R pixel of the imaging sensor 48. The imaging control unit 55 further executes second imaging for capturing one frame of the second observation target or the third observation target being illuminated with the second blue light BL, the green light G, and the red light R, which are simultaneously emitted during the second light emission. As a result, during the second imaging, a B2n image signal is output from a B pixel, a G2n image signal is output from a G pixel, and an R2n image signal is output from an R pixel of the imaging sensor 48.

The B1n image signal, the G1n image signal, the R1n image signal, the B2n image signal, the G2n image signal, and the R2n image signal each correspond to a second spectral image or a third spectral image of the present invention. Thus, a plurality of second spectral images or third spectral images include the B1n image signal, the G1n image signal, the R1n image signal, the B2n image signal, the G2n image signal, and the R2n image signal.

In this embodiment, the photographic subjects in both the oxygen saturation mode and the ischemia evaluation mode are the first observation target. However, the photographic subjects in the oxygen saturation mode and the ischemia evaluation mode do not need to be the same, and different observation targets may be used as the photographic subjects in the oxygen saturation mode and the ischemia evaluation mode. In addition, the first observation target in the oxygen saturation mode or the ischemia evaluation mode and the second observation target in the reference-value calculation mode are different photographic subjects. However, the photographic subjects in these modes do not need to be different, and the same observation target may be used as the photographic subjects in some observation modes.

The imaging signal (analog signal) output from the imaging sensor 48 is input to an A/D converter (not illustrated) through a scope cable. The A/D converter converts the imaging signal (analog signal) into an image signal (digital signal) corresponding to the voltage level thereof. The converted image signal is input to the lumen processor apparatus 23 via the connector portion.

In the lumen processor apparatus 23, a program related to a process for calculating a first actual measurement value of oxygen saturation, a process for calculating a first reference value of the oxygen saturation, a process for calculating a relative value of the first actual measurement value, a process for generating an evaluation oxygen-saturation image, and the like is incorporated in a memory (not illustrated). The program is operated by a control unit 56, which is constituted by a processor, to implement the functions of a central control unit 56a, an image acquisition unit 57, an image processing unit 58, and a display control unit 59.

As illustrated in FIG. 4, the lumen processor apparatus 23 includes the control unit 56, the image acquisition unit 57, the image processing unit 58, and the display control unit 59. The image acquisition unit 57 includes a DSP (Digital Signal Processor) 61, a noise reduction unit 62, and a conversion unit 63. The control unit 56 includes the central control unit 56a. The display control unit 59 includes a display image selection unit 59a.

The DSP 61 performs various types of signal processing, such as defect correction processing, offset processing, gain correction processing, linear matrix processing, gamma conversion processing, demosaicing processing, and YC conversion processing, on the received image signal. The defect correction processing corrects a signal of a defective pixel of the imaging sensor 48. The offset processing removes a dark current component from the image signal subjected to the defect correction processing and sets an accurate zero level. The gain correction processing multiplies an image signal of each color, which is subjected to the offset processing, by a specific gain to adjust the signal level of each image signal. The linear matrix processing enhances the color reproducibility of the image signal of each color subjected to the gain correction processing.

The gamma conversion processing adjusts the brightness and color saturation of each image signal subjected to the linear matrix processing. The demosaicing processing (also referred to as isotropic processing) generates a signal of a missing color of each pixel to interpolate the image signal subjected to the gamma conversion processing. The demosaicing processing allows all the pixels to have signals of the respective colors of R, G, and B. The DSP 61 performs YC conversion processing to convert each image signal subjected to the demosaicing processing into a luminance signal Y and color difference signals Cb and color difference signals Cr, and outputs these signals to the noise reduction unit 62.

The noise reduction unit 62 performs noise reduction processing on the image signal from the DSP 61. The noise reduction processing is, for example, a moving-average method, a median filter method, or the like. The image signal with noise reduced by the noise reduction processing is input to the conversion unit 63. The conversion unit 63 reconverts the luminance channel Y, the color difference channel Cb, and the color difference channel Cr, which are subjected to the noise reduction processing, into an image of the respective colors of R, G, and B.

The central control unit 56a controls the light source control unit 42 and the imaging control unit 55 to execute the normal observation mode, the oxygen saturation mode, the ischemia evaluation mode, and the reference-value calculation mode. The central control unit 56a is electrically connected to the image processing unit 58 and notifies the image processing unit 58 of which of the normal observation mode, the oxygen saturation mode, the ischemia evaluation mode, and the reference-value calculation mode has been executed.

The central control unit 56a captures a normal image in the normal observation mode. In the capturing of a normal image, the light source control unit 42 is controlled to emit illumination light for the normal image. Accordingly, during the capturing of a normal image, an image of the observation target illuminated with the first blue light BS, the green light G, and the red light R is captured to obtain a Bc image signal, a Gc image signal, and an Rc image signal.

In the oxygen saturation mode or the ischemia evaluation mode, the central control unit 56a controls the light source control unit 42 to alternately execute emissions of illumination light, namely, the first light emission and the second light emission, and controls the imaging control unit 55 in accordance with the first light emission and the second light emission to alternately execute the first imaging and the second imaging. As a result, in a case where the first light emission and the first imaging are executed, an image of the first observation target illuminated with the first blue light BS, the green light G, and the red light R is captured to obtain a B1m image signal, a G1m image signal, and an R1m image signal. In a case where the second light emission and the second imaging are executed, an image of the first observation target illuminated with the second blue light BL, the green light G, and the red light R is captured to obtain a B2m image signal, a G2m image signal, and an R2m image signal. The B1m image signal, the G1m image signal, and the R1m image signal, and the B2m image signal, the G2m image signal, and the R2m image signal are two consecutive sets of image signals.

In the reference-value calculation mode, as in the oxygen saturation mode or the ischemia evaluation mode, the central control unit 56a controls the light source control unit 42 to alternately execute emissions of illumination light, namely, the first light emission and the second light emission, and controls the imaging control unit 55 in accordance with the first light emission and the second light emission to alternately execute the first imaging and the second imaging. As a result, in a case where the first light emission and the first imaging are executed, an image of the second observation target or the third observation target illuminated with the first blue light BS, the green light G, and the red light R is captured to obtain a B1n image signal, a G1n image signal, and an R1n image signal. In a case where the second light emission and the second imaging are executed, an image of the second observation target or the third observation target illuminated with the second blue light BL, the green light G, and the red light R is captured to obtain a B2n image signal, a G2n image signal, and an R2n image signal. The B1n image signal, the G1n image signal, and the R1n image signal, and the B2n image signal, the G2n image signal, and the R2n image signal are two consecutive sets of image signals.

Figure 10:
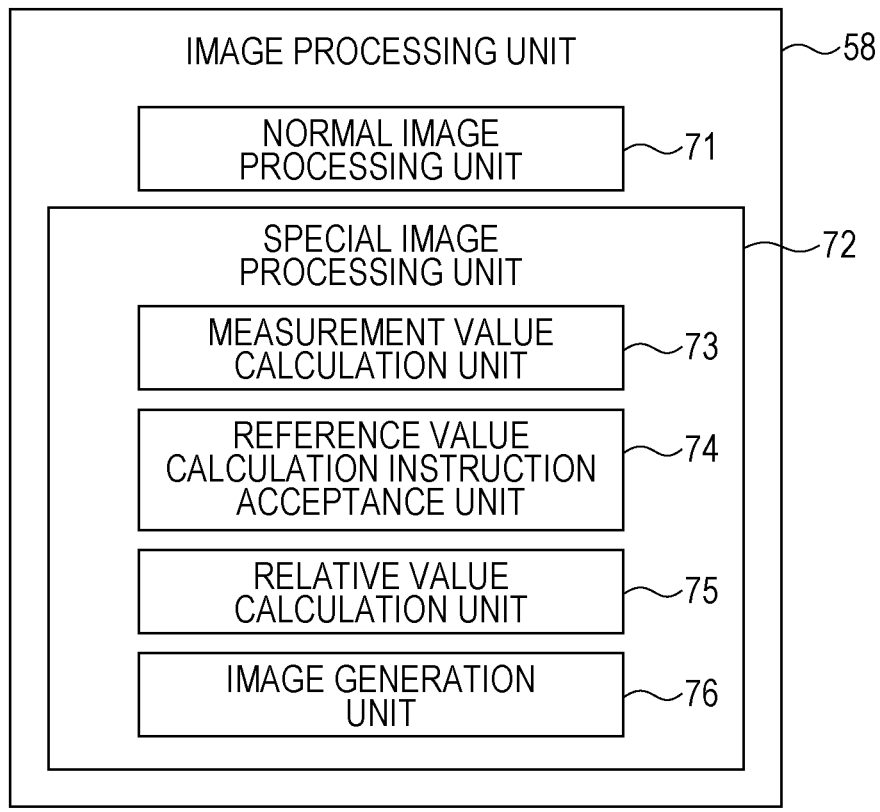
FIG. 10 is a block diagram illustrating functions of an image processing unit.

As illustrated in FIG. 10, the image processing unit 58 includes a normal image processing unit 71 and a special image processing unit 72 and performs predetermined image processing on an image signal from the lumen endoscope apparatus 22. The normal image processing unit 71 performs predetermined image processing on an image signal obtained in the normal observation mode to generate a normal image.

The special image processing unit 72 processes an image obtained in the oxygen saturation mode, the ischemia evaluation mode, or the reference-value calculation mode. The special image processing unit 72 includes a measurement value calculation unit 73, a reference value calculation instruction acceptance unit 74, a relative value calculation unit 75, and an image generation unit 76. The special image processing unit 72 performs a series of processes based on an image signal input from the lumen endoscope apparatus 22 and calculates a reference value or calculates a relative value. Then, the relative value is used to generate an observation image or an evaluation image.

The measurement value calculation unit 73 includes a function of calculating an actual measurement value of the oxygen saturation of a tissue to be observed on the basis of a plurality of spectral images. In a case where the spectral images are first spectral images, the calculated oxygen saturation is set as a first actual measurement value. In a case where the spectral images are second spectral images, the calculated oxygen saturation is set as a second actual measurement value. Thus, the oxygen saturation calculated on the basis of the plurality of first spectral images is a first actual measurement value of oxygen saturation. The oxygen saturation calculated on the basis of the plurality of second spectral images is a second actual measurement value of oxygen saturation. Also, in a case where the spectral images are third spectral images, the oxygen saturation calculated on the basis of the third spectral images is a third actual measurement value of oxygen saturation.

The measurement value calculation unit 73 further includes a function of calculating a reference value of the oxygen saturation of the tissue to be observed on the basis of a plurality of spectral images. The reference value is calculated using an actual measurement value calculated based on a plurality of spectral images. In a case where the spectral images are second spectral images, the calculated oxygen saturation is set as a second actual measurement value, and a reference value calculated using the second actual measurement value is set as a first reference value.

The reference value calculation instruction acceptance unit 74 accepts an instruction to calculate a reference value. The relative value calculation unit 75 calculates a relative value of the first actual measurement value on the basis of the first actual measurement value of the oxygen saturation and the first reference value of the oxygen saturation, which are calculated by the measurement value calculation unit 73. The image generation unit 76 generates an image of the relative value of the first actual measurement value on the basis of an evaluation color table to generate an evaluation image. The image generation unit 76 further generates an image of the actual measurement value on the basis of an observation color table to generate an observation image.

Figure 11:
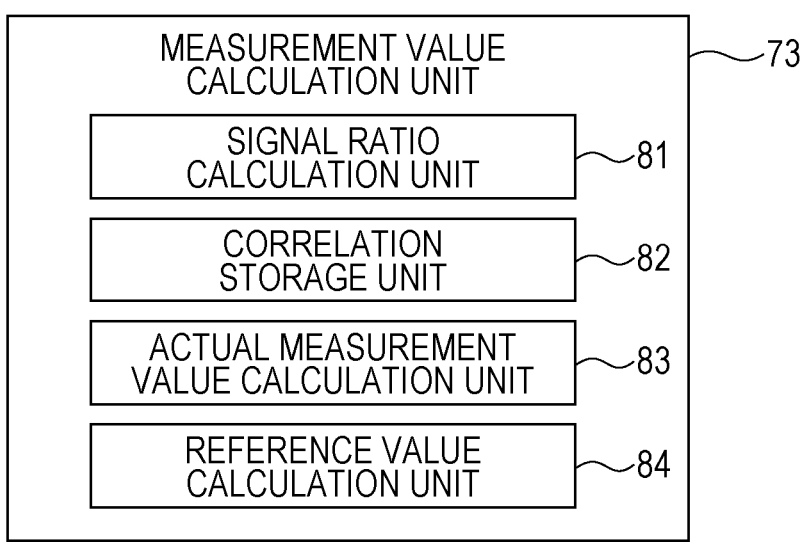
FIG. 11 is a block diagram illustrating functions of a measurement value calculation unit.

As illustrated in FIG. 11, the measurement value calculation unit 73 includes a signal ratio calculation unit 81, a correlation storage unit 82, an actual measurement value calculation unit 83, and a reference value calculation unit 84.

The signal ratio calculation unit 81, the correlation storage unit 82, and the actual measurement value calculation unit 83 calculate the first actual measurement value of the oxygen saturation on the basis of the plurality of first spectral images, calculate the second actual measurement value of the oxygen saturation on the basis of the plurality of second spectral images, and calculate the third actual measurement value of the oxygen saturation on the basis of the plurality of third spectral images. The reference value calculation unit 84 calculates a reference value from the second actual measurement value or the third actual measurement value. The reference value calculation unit 84 calculates the first reference value using the second actual measurement value and calculates the second reference value using the third actual measurement value. Thus, the reference value calculation unit 64 calculates the first reference value of the oxygen saturation of the tissue to be observed on the basis of the plurality of second spectral images.

The signal ratio calculation unit 81 determines a signal ratio having dependence on both the blood volume and the oxygen saturation using the plurality of first spectral images acquired in the oxygen saturation mode or the ischemia evaluation mode and obtained by capturing an image of the first observation target that includes a lesion.

The signal ratio calculation unit 81 calculates the signal ratio between pixels located at the same position in the first spectral images acquired in the oxygen saturation mode or the ischemia evaluation mode, that is, the B1m image signals, the G1m image signals, and the R1m image signals in the first imaging and the B2m image signals, the G2m image signals, and the R2m image signals in the second imaging. The signal ratio is calculated for all the pixels of the image signals. Thus, the oxygen saturation is calculated for each pixel. In this embodiment, the signal ratio calculation unit 81 determines a signal ratio $B2m/(B1m+G1m)$ between the sum of a blue signal B1m in the first imaging and a green signal G1m in the first imaging and a blue signal B2m in the second imaging, and a signal ratio $R1m/G1m$ between the green signal G1m and a red signal R1m in the first imaging.

The signal ratios may be determined for only pixels of a blood vessel portion in the image signals. In this case, the blood vessel portion is specified based on the difference between the image signals of the blood vessel portion and the image signals of the other portion.

Figure 12:
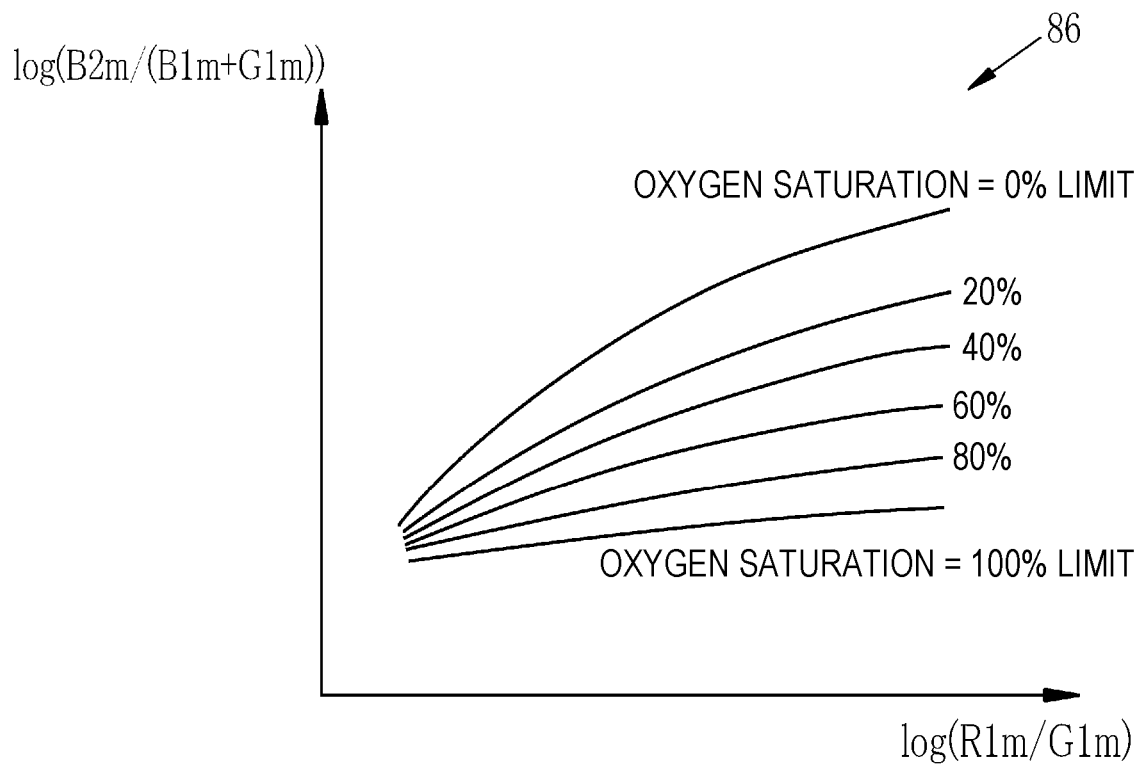
FIG. 12 is a graph illustrating a correlation between oxygen saturation and signal ratios.

The correlation storage unit 82 stores a correlation between the signal ratios $B2m/(B1m+G1m)$ and $R1m/G1m$ and the oxygen saturation. The correlation between the signal ratios and the oxygen saturation is stored in a two-dimensional table 86 illustrated in FIG. 12 in which contour lines for oxygen saturation are defined in a two-dimensional space. The positions and shapes of the contour lines are obtained by a physical simulation of light scattering and are defined so as to vary depending on the blood volume. For example, a change in blood volume may cause the spacing between the contour lines to increase or decrease. The signal ratio $B2m/(B1m+G1m)$ and the signal ratio $R1m/G1m$ are stored on log scale.

Figure 13:
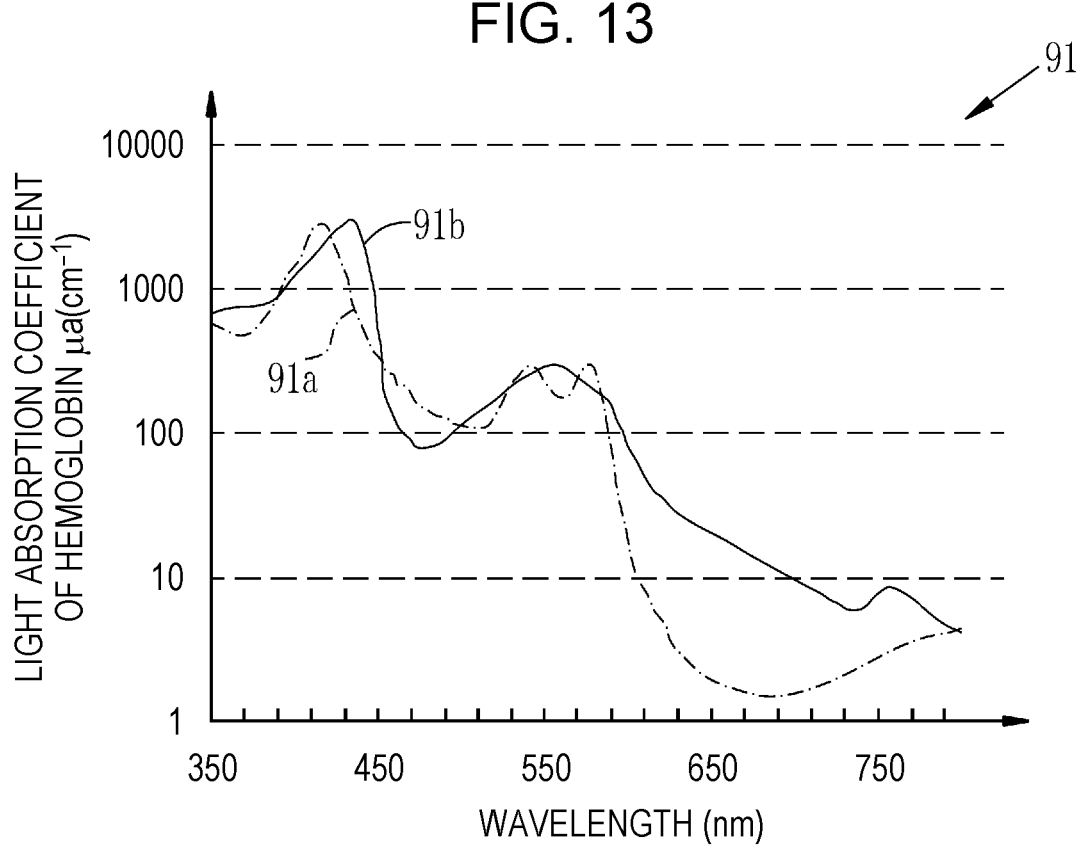
FIG. 13 is a graph illustrating light absorption coefficients of hemoglobin.

The correlation described above is closely related with the light absorption properties or light scattering properties of oxyhemoglobin or deoxyhemoglobin as illustrated in FIG. 13. A graph 91 illustrates a light absorption coefficient of oxyhemoglobin 91a and a light absorption coefficient of deoxyhemoglobin 91b. As illustrated in FIG. 13, for example, information on the oxygen saturation is easily obtained at a wavelength having a large difference in light absorption coefficient, such as 470 nm. However, a blue signal including a signal corresponding to 470 nm light has high dependence on the blood volume as well as the oxygen saturation. Accordingly, the signal ratio B2m/(B1m+G1m) and the signal ratio R1m/G1m, which are obtained from, in addition to the blue signal B1m, the red signal R1m corresponding to light that mainly changes depending on the blood volume and the green signal G1m serving as a reference signal of the blue signal B2m and the red signal R1m, are used, thereby making it possible to accurately determine the oxygen saturation without depending on the blood volume.

In addition, the following points are obtained from the wavelength dependence of the light absorption coefficient of hemoglobin of the tissue being observed.

(1) The light absorption coefficient greatly changes around a wavelength of 470 nm (for example, in the blue wavelength range having a center wavelength of 470 nm±10 nm) in accordance with a change in oxygen saturation.

(2) When averaged over the green wavelength range of 540 to 580 nm, the light absorption coefficient is less sensitive to changes in oxygen saturation.

(3) In the red wavelength range of 590 to 700 nm, although the light absorption coefficient appears to greatly change with the oxygen saturation, the light absorption coefficient has very small values and is thus eventually less sensitive to changes in oxygen saturation.

The actual measurement value calculation unit 83 (FIG. 11) determines the oxygen saturation at each pixel using the correlation stored in the correlation storage unit 82 and the signal ratio B2m/(B1m+G1m) and the signal ratio R1m/G1m determined by the signal ratio calculation unit 81. As to the oxygen saturation, first, as illustrated in FIG. 14, a correspondence point P corresponding to the signal ratio B2m*/(B1m*+G1m*) and the signal ratio R1m*/G1m*, which are determined by the signal ratio calculation unit 81, in the two-dimensional space is specified.

Figure 14:
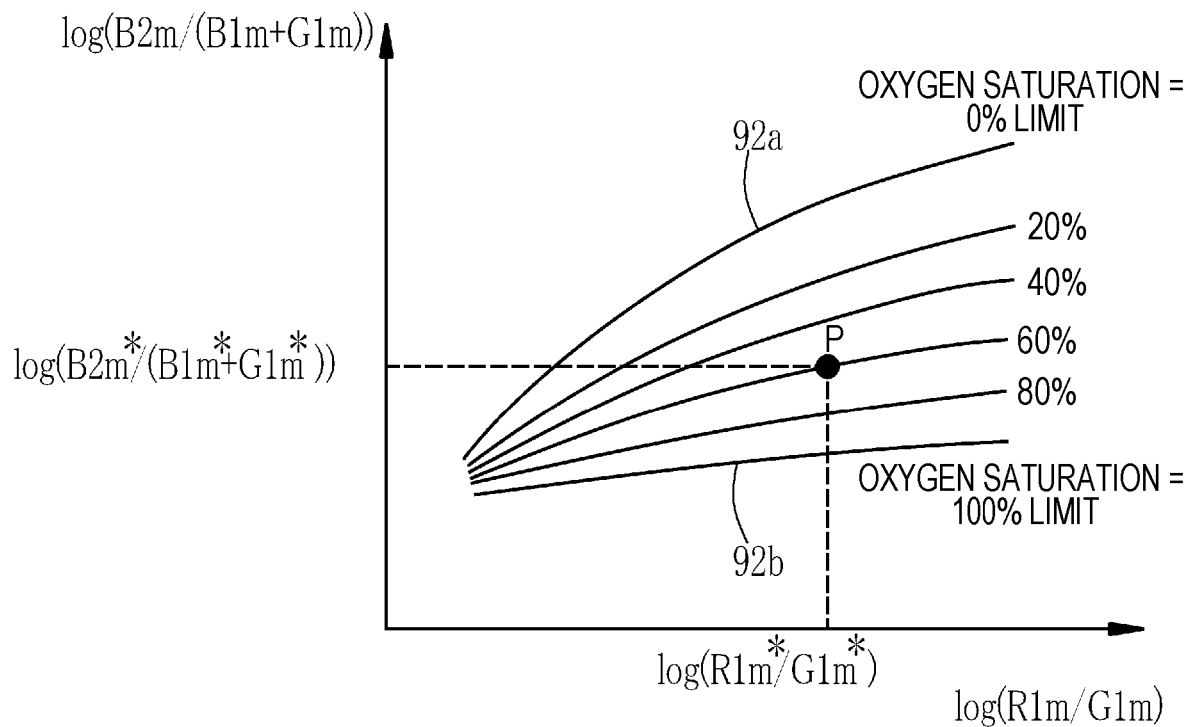
FIG. 14 is an explanatory diagram describing a method for determining an actual measurement value of oxygen saturation from the signal ratios in the graph illustrated in FIG. 12.

Then, as illustrated in FIG. 14, if the correspondence point P is located between a lower-limit line 92*a* representing "oxygen saturation=0% limit" and an upper-limit line 92*b* representing "oxygen saturation=100% limit", the percentage value indicated by the contour line where the correspondence point P is located is the oxygen saturation. For example, in the case of FIG. 14, since the contour line where the correspondence point P is located indicates 60%, the oxygen saturation is 60%. In a case where the correspondence point P is outside the range between the lower-limit line 92*a* and the upper-limit line 92*b*, the oxygen saturation is set to 0% when the correspondence point P is located above the lower-limit line 92*a*, and the oxygen saturation is set to 100% when the correspondence point P is located below the upper-limit line 92*b*. In a case where the correspondence point P is outside the range between the lower-limit line 92*a* and the upper-limit line 92*b*, the reliability of the oxygen saturation at the pixel in question may be lowered, and the oxygen saturation may not be displayed.

In the oxygen saturation mode, the image generation unit 76 generates an image of the first actual measurement value of the oxygen saturation calculated in the way described above on the basis of an observation color table to generate an observation image.

Figure 15:
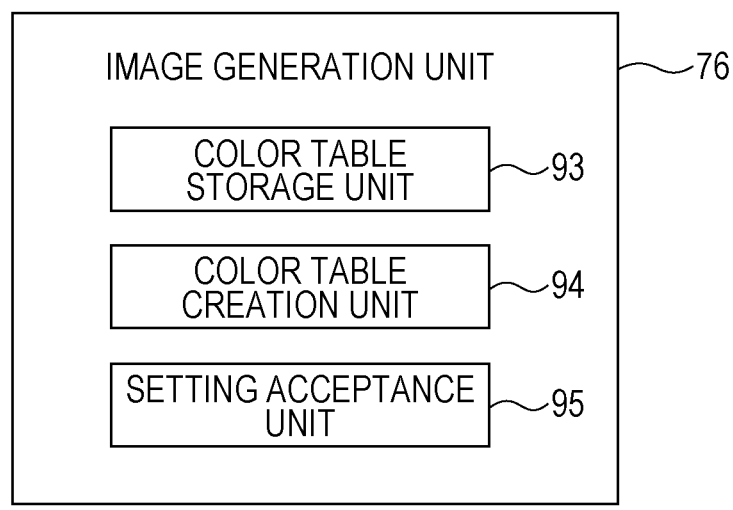
FIG. 15 is a block diagram illustrating functions of an image generation unit.

As illustrated in FIG. 15, the image generation unit 76 includes a color table storage unit 93, a color table creation unit 94, and a setting acceptance unit 95. The image generation unit 76 generates an image of the first actual measurement value determined by the actual measurement value calculation unit 83 on the basis of an observation color table to generate an observation image. The observation color table is a color table for an observation image, in which the oxygen saturation and color information of the observation image are associated with each other. The observation color table is stored in the color table storage unit 93.

Figure 16:
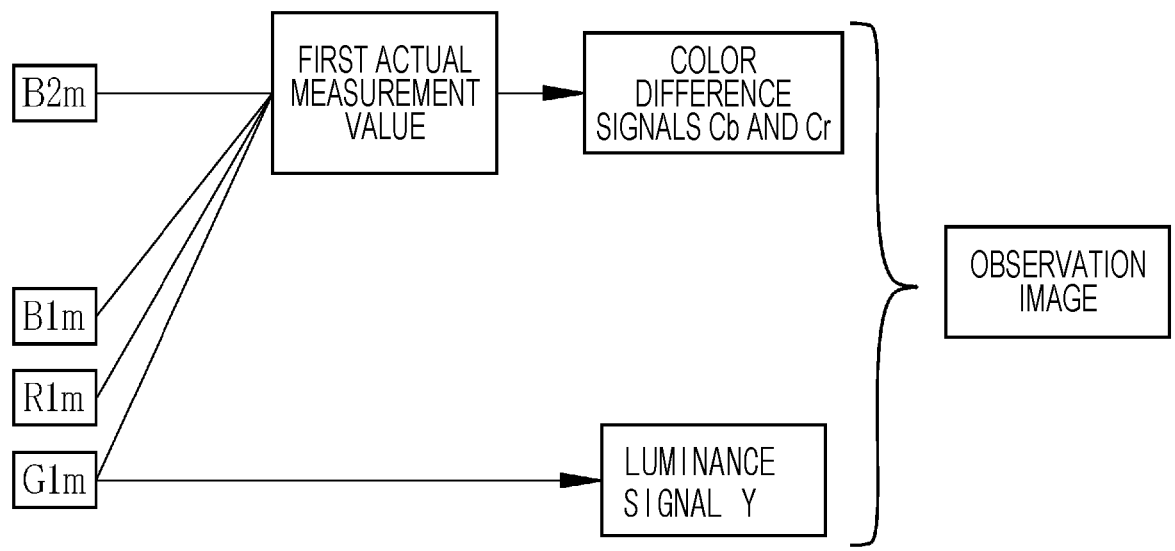
FIG. 16 is a block diagram illustrating a procedure for creating an observation image.

As illustrated in FIG. 16, in the case of a video signal to be output to the monitor, the observation image is composed of a video signal including a luminance signal Y, a color difference signal Cb, and a color difference signal Cr. The observation image is generated by assigning a pixel value of a G1m image signal in the first imaging to the luminance signal Y and assigning the calculated first actual measurement value of the oxygen saturation to the color difference signals Cb and Cr. Since the pixel value of the G1m image signal in the first imaging corresponds to reflected light in a wavelength range in which light is slightly strongly absorbed by hemoglobin, it is possible to visually recognize irregularities of mucous membranes, blood vessels, and the like from an image based on the pixel value. Accordingly, assigning a pixel value of a G1m image signal to the luminance signal Y makes it possible to define the overall brightness of the observation image.

Figure 17:
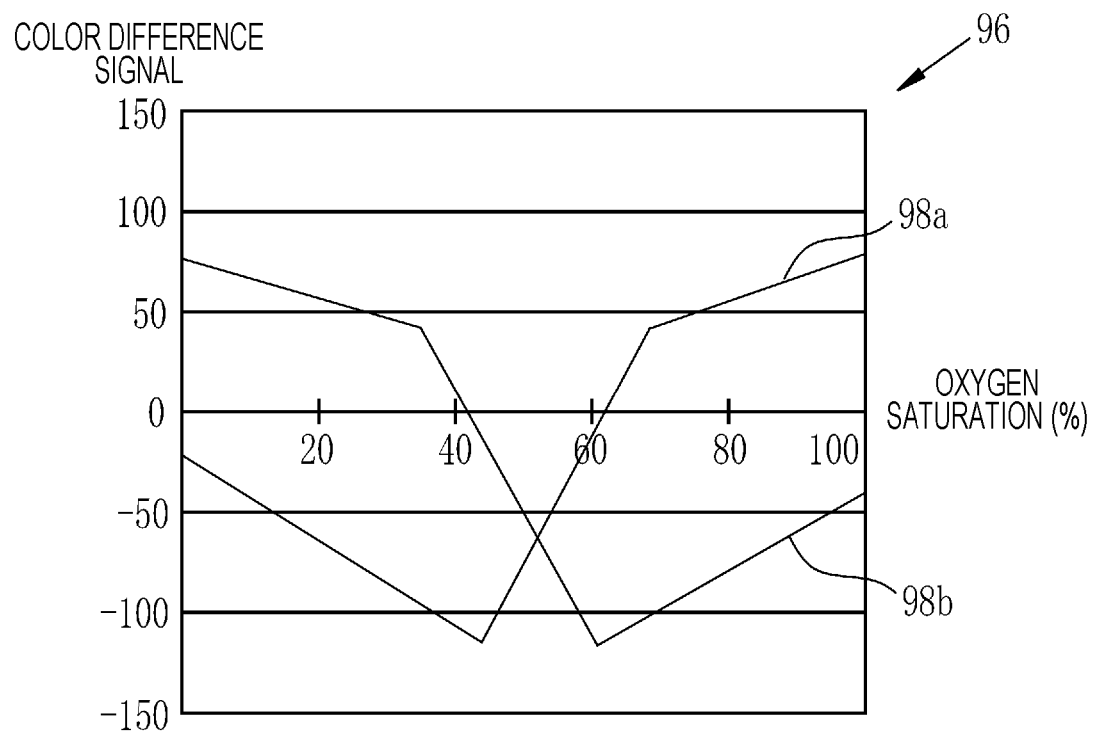
FIG. 17 is an explanatory diagram of an observation color table.

The color difference signals Cb and Cr are assigned signal values corresponding to the first actual measurement value of the oxygen saturation in accordance with, for example, an observation color table 96 illustrated in FIG. 17. The observation color table 96 is defined such that a color difference signal Cr 98*a* has a positive signal value and a color difference signal Cb 98*b* has a negative signal value in a region where the oxygen saturation is high, whereas the color difference signal Cr 98*a* has a negative signal value and the color difference signal Cb 98*b* has a positive signal value in a region where the oxygen saturation is low. The observation color table 96 is further defined such that the magnitude relationship between the signal value of the color difference signal Cr 98*a* and the signal value of the color difference signal Cb 98*b* is reversed at an oxygen saturation of 50%. Thus, as the oxygen saturation increases from low to high, the color changes from blue to light blue, green, yellow, orange, and red in this order.

Next, calculation of a reference value will be described. The calculation of a reference value starts when, for example, the mode is switched to the reference-value calculation mode in response to the reference value calculation instruction acceptance unit 74 accepting an instruction from the operator. Specifically, the instruction from the operator is, for example, to press the scope button, which is the reference value calculation instruction portion 28*b*. During the examination, the operator sets, as an observation target, a region for which the value of the oxygen saturation of the tissue to be observed is desired to be used as a reference value, and then presses the scope button, which is the reference value calculation instruction portion 28*b*. As a result, the observation mode is switched to the reference-value calculation mode, and a plurality of second spectral images are acquired by capturing an image of the observation target. A second actual measurement value is calculated on the basis of the plurality of second spectral images, and a first reference value is calculated on the basis of the second actual measurement value.

The second actual measurement value is determined by processing the second actual measurement value of the oxygen saturation at each pixel in a manner similar to that for the calculation of the first actual measurement value using the acquired plurality of second spectral images. More specifically, the signal ratio calculation unit 81 uses the plurality of second spectral images obtained in response to the operation of the reference value calculation instruction portion 28b to determine a signal ratio having dependence on both the blood volume and the oxygen saturation. The signal ratio based on the second spectral images is a second actual measurement value of the oxygen saturation of the second observation target. Specifically, the plurality of second spectral images are subjected to determination of the second actual measurement value using the signal ratio B2n/(B1n+G1n) and the signal ratio R1n/G1n obtained by the signal ratio calculation unit 81 and the correlation and the two-dimensional space (see FIG. 14) stored in the correlation storage unit 82. The calculation of the oxygen saturation is performed on each pixel of the second spectral images. Thus, the oxygen saturation is calculated for pixels located at the same location in the plurality of second spectral images to calculate the oxygen saturation for each pixel location.

The reference value calculation unit 84 averages the second actual measurement values of the oxygen saturation at the respective pixel locations, which are calculated by the actual measurement value calculation unit 83, in, for example, the range of one spectral image or the like. The calculated averaged value is set as a first reference value of the oxygen saturation. When the first reference value is calculated, the calculated first reference value is sent to the relative value calculation unit 75, and the relative value calculation unit 75 calculates a relative value using the calculated first reference value.

The reference value calculation unit 84 may calculate the first reference value using a plurality of sets of second spectral images. In this case, for example, a plurality of frames, each frame representing one set of spectral images, may be set, and the first reference value of the oxygen saturation of the entire plurality of frames may be calculated by determining an average value of oxygen saturation for each frame, adding the determined average values together, and dividing the sum by the number of frames. Alternatively, an average value may be determined for pixels at the same position, and average values may be averaged over a range of the spectral images. Also for a first actual measurement value of oxygen saturation based on the first spectral images, an average value may be determined for pixels at the same position over a plurality of frames, and a first actual measurement value of hemoglobin concentration and oxygen saturation may be determined.

The reference value may be acquired by using a method other than the method in which the reference value is calculated whenever necessary. Specifically, for example, at the beginning of a surgical operation, a typical value of oxygen saturation indicated by a normal mucous membrane of the digestive tract from the mouth to the anus may be set as a default first reference value in advance. Alternatively, the previous first reference value may be stored, and this first reference value may be used until the operator gives an instruction to calculate a first reference value. The first reference value may be updated in response to the operator giving an instruction to calculate a first reference value. Alternatively, switching to the reference-value calculation mode or calculation of a first reference value may be performed by using any other method instead of in accordance with an instruction from the operator. Specifically, for example, when the mode switch 28a sets the ischemia evaluation mode, the ischemia evaluation mode may be automatically switched to the reference-value calculation mode, and, after calculation of a first reference value is performed and the first reference value is set, the reference-value calculation mode may be automatically switched to the ischemia evaluation mode.

Figure 18:
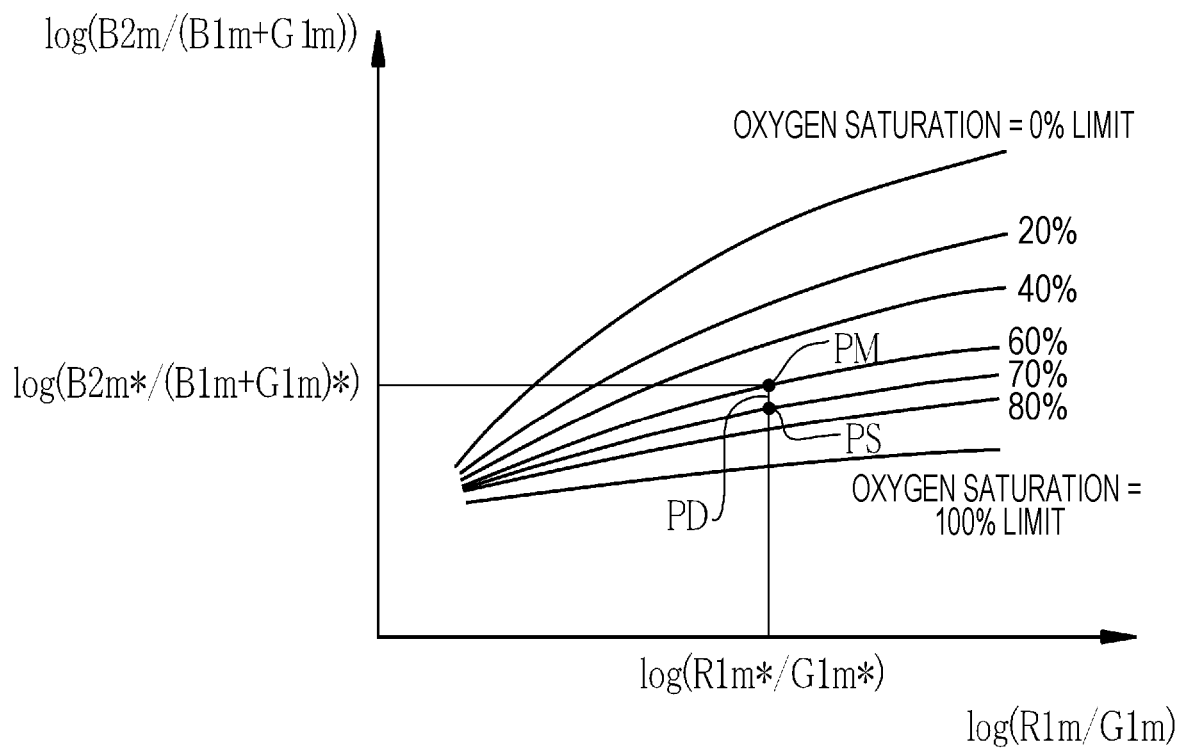
FIG. 18 is an explanatory diagram describing a method for determining a relative value of oxygen saturation from the signal ratios in the graph illustrated in FIG. 12.

Next, calculation of a relative value of a first actual measurement value with reference to a first reference value will be described. The relative value calculation unit 75 uses each first actual measurement value of oxygen saturation based on the first spectral images and the first reference value of the oxygen saturation to calculate a relative value of the first actual measurement value on the basis of the first spectral images. For example, the relative value of the first actual measurement value can be a value obtained by subtracting the first reference value from the first actual measurement value. Thus, the relative value calculation unit 75 calculates a relative value of the first actual measurement value with reference to the first reference value. Specifically, if the first actual measurement value of the oxygen saturation based on the first spectral images is represented by $StO_2(MV)$ and the first reference value of the oxygen saturation is represented by $StO_2(STD)$, the relative value $\Delta StO_2$ of the first actual measurement value is a value obtained by subtracting the first reference value $StO_2(STD)$ of the oxygen saturation from the first actual measurement value $StO_2(MV)$ of the oxygen saturation. Thus, as illustrated in FIG. 18, the relative value $\Delta StO_2$ of the first actual measurement value is a difference PD in a case where a first reference value PS of oxygen saturation and a first actual measurement value PM of oxygen saturation are set. When the relative value $\Delta StO_2$ of the first actual measurement value is expressed by an equation, the following Equation (1) is obtained. The relative value $\Delta StO_2$ of the first actual measurement value is a relative value calculated with reference to the first reference value and thus has the same unit (%) as that of the oxygen saturation.

$$StO_2(MV)-StO_2(STD)=\Delta StO_2 \qquad (1)$$

Next, generation of an evaluation image from a generated image of the relative value $\Delta StO_2$ of the first actual measurement value will be described. The image generation unit 76 generates an image of the relative value $\Delta StO_2$ of the first actual measurement value, which is determined by the relative value calculation unit 75, on the basis of the evaluation color table to generate an evaluation image. An evaluation color table 97 is a color table for an evaluation image storing pseudo-color information that changes in accordance with the relative value $\Delta StO_2$ of the first actual measurement value. The color table creation unit 94 creates the evaluation color table 97 in which the relative value $\Delta StO_2$ of the first actual measurement value and color information of the evaluation image are associated with each other. The evaluation color table 97 is a general name and includes an evaluation color table 97a, an evaluation color table 97b, and the like.

Figure 19:
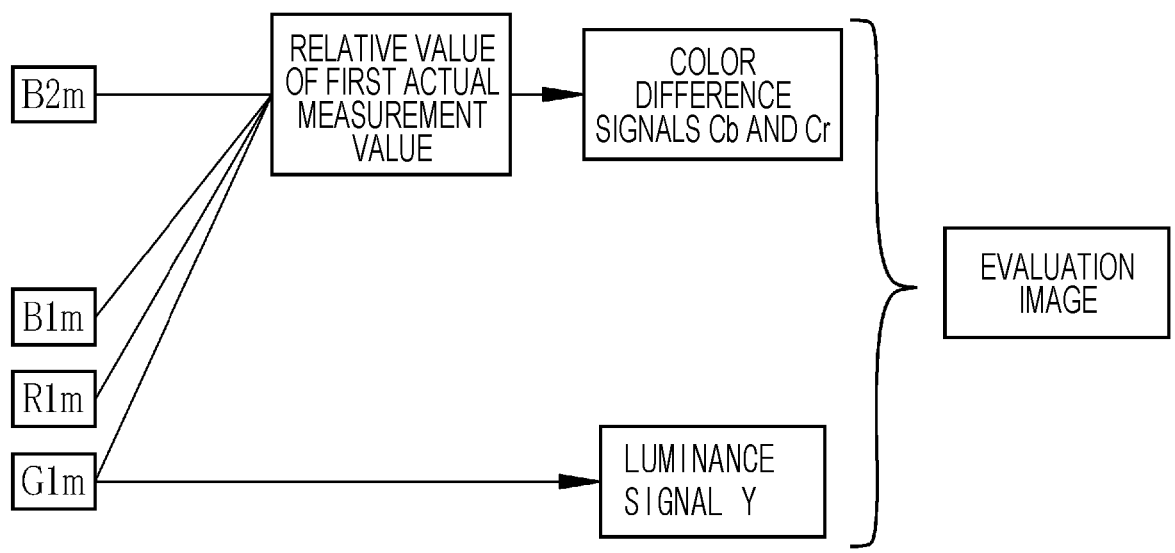
FIG. 19 is a block diagram illustrating a procedure for creating an evaluation image.

As illustrated in FIG. 19, in the case of a video signal to be output to the monitor, the evaluation image is composed of a video signal including a luminance signal Y, a color difference signal Cb, and a color difference signal Cr. The evaluation image is generated by assigning a pixel value of a G1m image signal in the first imaging to the luminance signal Y and assigning the calculated relative value $\Delta StO_2$ of the first actual measurement value to the color difference signals Cb and Cr. Since the pixel value of the G1m image signal in the first imaging corresponds to reflected light in a wavelength range in which light is slightly strongly absorbed by hemoglobin, it is possible to visually recognize irregularities of mucous membranes, blood vessels, and the like from an image based on the pixel value. Accordingly, assigning a pixel value of a G1m image signal to the luminance signal Y makes it possible to define the overall brightness of the evaluation image.

Figure 20:
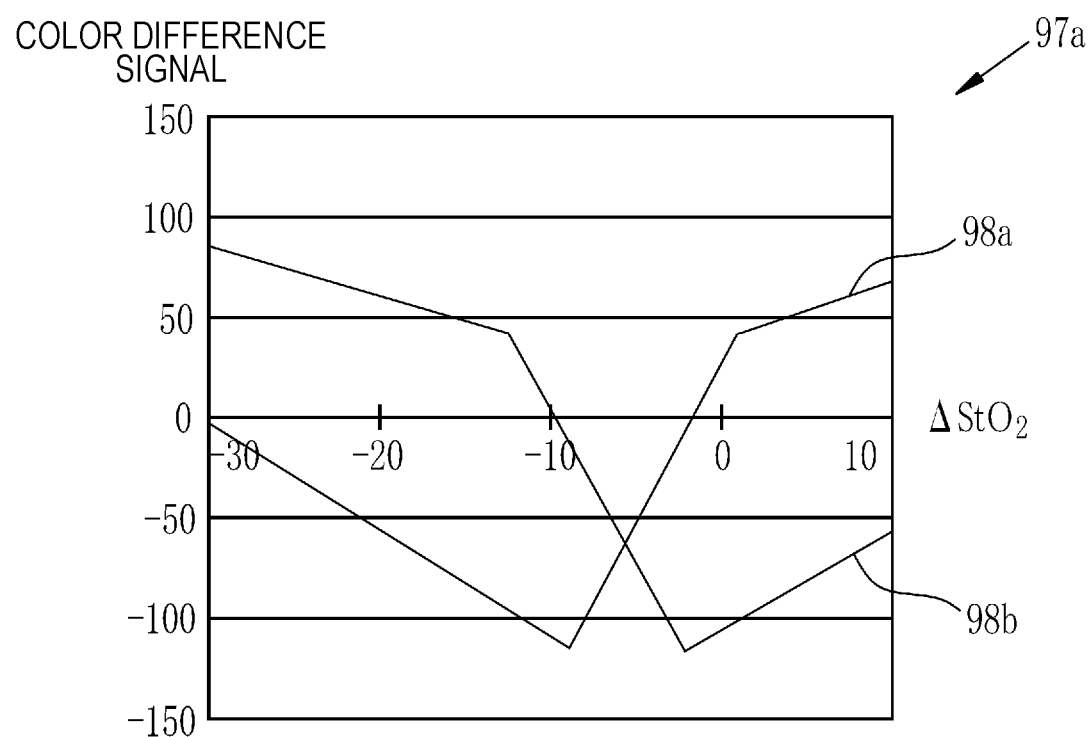
FIG. 20 is an explanatory diagram of an evaluation color table.

The color difference signals Cb and Cr are assigned signal values corresponding to the relative value $\Delta StO_2$ of the first actual measurement value in accordance with, for example, the evaluation color table 97a illustrated in FIG. 20. The evaluation color table 97a is defined such that a color difference signal Cr 98a has a positive signal value and a color difference signal Cb 98b has a negative signal value in a region where the relative value $\Delta StO_2$ of the first actual measurement value is large, whereas the color difference signal Cr 98a has a negative signal value and the color difference signal Cb 98b has a positive signal value in a region where the relative value $\Delta StO_2$ of the first actual measurement value is small. Thus, as the relative value $\Delta StO_2$ of the first actual measurement value increases from low to high, the color changes from blue to light blue, green, yellow, orange, and red in this order. The evaluation color table 97a is further defined such that the magnitude relationship between the signal value of the color difference signal Cr 98a and the signal value of the color difference signal Cb 98b is reversed in the range of the relative value $\Delta StO_2$ of the first actual measurement value from −10% to 0%, for example.

In addition, the evaluation color table 97a is created such that, for example, the range from the lower limit value of the relative value $\Delta StO_2$ of the first actual measurement value displayed in blue in the evaluation image to the upper limit value of the relative value $\Delta StO_2$ of the first actual measurement value displayed in red corresponds to the range of the relative value $\Delta StO_2$ of the first actual measurement value. The relative value $\Delta StO_2$ of the first actual measurement value is a relative value with reference to the first reference value. Thus, the evaluation color table 97 is a color table in which color changes in a narrow range in accordance with the relative value $\Delta StO_2$ of the first actual measurement value. With the evaluation color table 97, in the ischemia evaluation mode, for example, the oxygen saturation of a region that does not include an arbitrary lesion or the like is set as a first reference value, and then an image of a region that includes the lesion or the like for which a subtle change in oxygen saturation is desired to be known is captured. As a result, an evaluation image in which a small change in oxygen saturation from the first reference value in the region that includes the lesion or the like is expressed as a color difference can be created and displayed on the monitor.

Further, the evaluation color table 97a is created such that, for example, the lower limit value of the relative value $\Delta StO_2$ of the first actual measurement value displayed in blue is set to −30% and the upper limit value of the relative value $\Delta StO_2$ of the first actual measurement value displayed in red is set to +10%. In addition, the evaluation color table 97a is created such that the relative value $\Delta StO_2$ of the first actual measurement value in a case where it is 0 (zero) and yellow in the evaluation image are associated with each other. The relative value $\Delta StO_2$ of the first actual measurement value in a case where it is 0 (zero) corresponds to an oxygen saturation having the same value as the first reference value $StO_2(STD)$ at the first actual measurement value $StO_2(MV)$.

The relative value $\Delta StO_2$ of the first actual measurement value in a case where it is 0 (zero) may be associated with a color other than yellow in the evaluation image, and is preferably associated with a specific color in the warm color system. Thus, an evaluation color table is crated in accordance with the relative value $\Delta StO_2$ of the first actual measurement value such that, in an evaluation image that uses first spectral images obtained by capturing an image of the first observation target, a high level of oxygen saturation and a low level of oxygen saturation are displayed in a color tone of the warm color system and a color tone of the cold color system, respectively, with the relative value $\Delta StO_2$ of the first actual measurement value in a case where it is 0 (zero) interposed therebetween. Accordingly, it is possible to create an evaluation image in which, in particular, the hypoxic side having low levels of oxygen saturation due to ischemia can be visually recognized with high contrast and color tone.

The observation image and/or the evaluation image created in the way described above are displayed on the monitor. As described above, the observation image is displayed on the monitor in the oxygen saturation mode, and the evaluation image is displayed on the monitor in the ischemia evaluation mode. The oxygen saturation mode and the ischemia evaluation mode are switched in accordance with an instruction from the mode switch 28a or the like. Accordingly, when the operator presses the scope button, which is the mode switch 28a of the lumen endoscope apparatus 22, the mode is switched, and the observation image and the evaluation image can be sequentially displayed on the monitor and compared.

Figure 21:
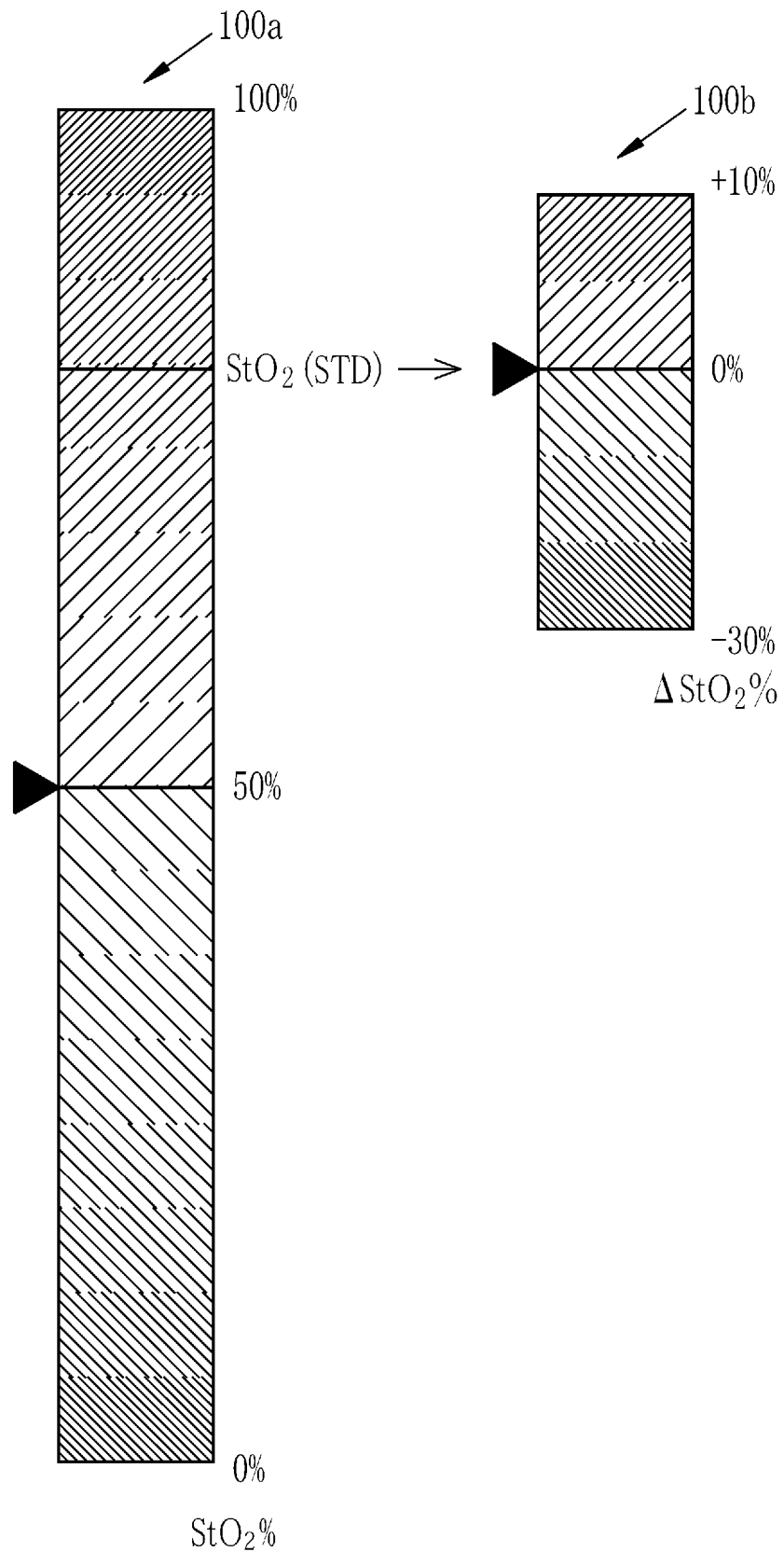
FIG. 21 is an explanatory diagram describing a difference in color bar indicating oxygen saturation between the observation image and the evaluation image.

In a case where the levels of oxygen saturation are presented in pseudo-color in the observation image using the observation color table 96 and the evaluation image using the evaluation color table 97, for example, the observation image, which presents a first actual measurement value on the basis of the observation color table 96, is an observation image in which the first actual measurement value is presented by a color bar 100a illustrated in the left portion of FIG. 21, and the evaluation image, which presents the relative value $\Delta StO_2$ of the first actual measurement value on the basis of the evaluation color table 97, is an evaluation image in which the relative value $\Delta StO_2$ of the first actual measurement value is presented by a color bar 100b illustrated in the right portion of FIG. 21.

The color bar 100a has colors corresponding to the levels of oxygen saturation (in FIG. 21, $StO_2$%) such that a lower portion of the color bar 100a indicates blue and corresponds to an oxygen saturation of 0%, an upper portion of the color bar 100a indicates red and corresponds to an oxygen saturation of 100%, and the center of the color bar 100a indicates green and corresponds to an oxygen saturation of 50%. In contrast, the color bar 100b illustrated in the right portion of FIG. 21 has colors corresponding to relative values $\Delta StO_2$ of first actual measurement values such that a lower portion of the color bar 100b indicates blue and has a lower limit corresponding to the relative value $\Delta StO_2$ of the first actual measurement value of −30%, an upper portion of the color bar 100b indicates red and has an upper limit corresponding to the relative value $\Delta StO_2$ of the first actual measurement value of +10%, and yellow in the color bar 100b corresponds to the relative value $\Delta StO_2$ of the first actual measurement value of 0%, that is, the first reference value $StO_2(STD)$. In the color bar 100b illustrated in the right portion of FIG. 21 in which colors are associated with the relative values $\Delta StO_2$ of the first actual measurement values, the upper limit value and lower limit value of the relative values $\Delta StO_2$ of the first actual measurement values and the upper limit and lower limit of the color bar 100b correspond to the upper limit value and lower limit value of the evaluation color table 97.

Thus, in a case where the observation color table 96 and the evaluation color table 97 have the same display color gradation, an evaluation image that is a pseudo-color image with high display gradation with respect to a change in oxygen saturation in the evaluation color table 97 is created. The evaluation image is obtained by calculating a relative value of the oxygen saturation of the tissue to be observed and generating an image of the relative values. The evaluation image is displayed on the monitor, thereby making it possible to clearly visually recognize a small change in oxygen saturation. Thus, the evaluation image serves as a clearer index for determining the boundary between a normal site and an ischemic site.

Figure 22:
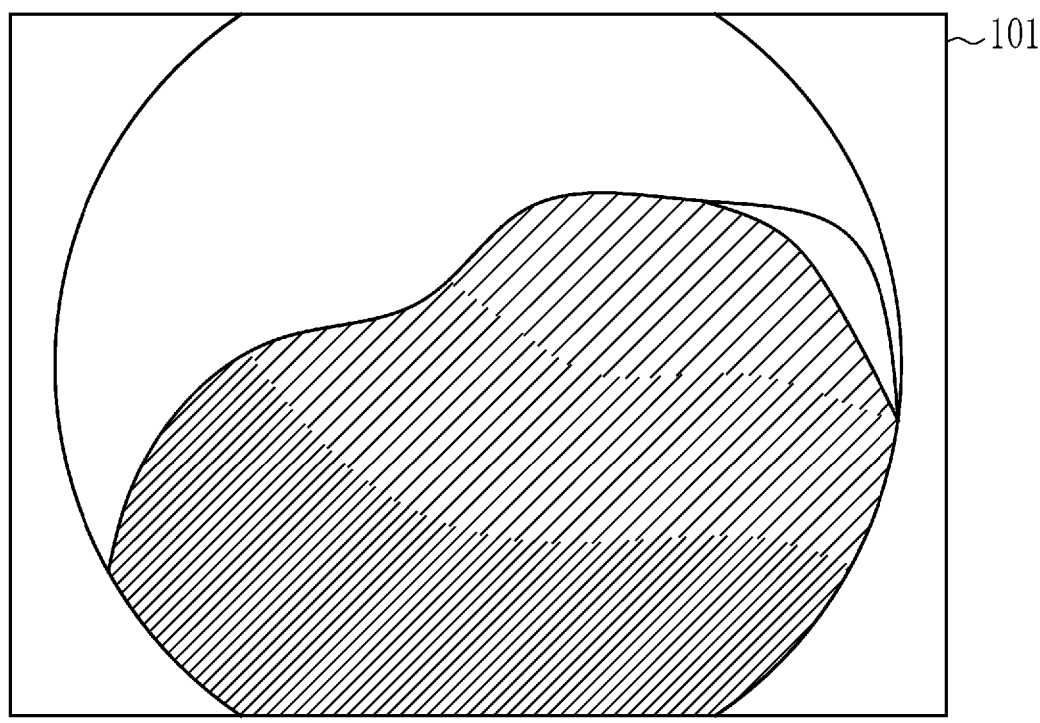
FIG. 22 is an image diagram of the observation image.
Figure 23:
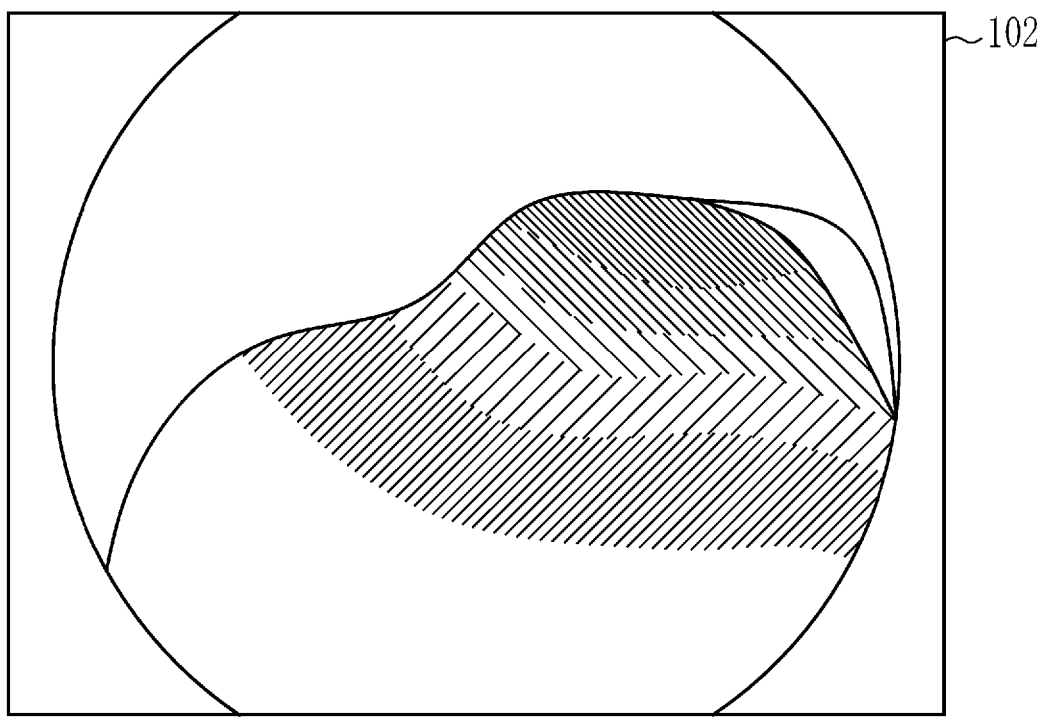
FIG. 23 is an image diagram of the evaluation image.

Next, display of the observation image and/or the evaluation image will be described. The display control unit 59 (see FIG. 4) controls an image to be displayed on the monitor (the display device 12). As illustrated in FIG. 22, in the oxygen saturation mode, in a case where an observation image 101 is generated, the display control unit 59 performs control to display at least the observation image 101 on the monitor. As illustrated in FIG. 23, in the ischemia evaluation mode, in a case where an evaluation image 102 is generated, the display control unit 59 performs control to display at least the evaluation image 102 on the monitor. The monitor displays at least the observation image 101 in the oxygen saturation mode and displays at least the evaluation image 102 in the ischemia evaluation mode. In the oxygen saturation mode, for example, the monitor may display the observation image 101 and the evaluation image 102, which has been created immediately before, in parallel. Likewise, in the ischemia evaluation mode, the monitor may display the evaluation image 102 and the observation image 101, which has been created immediately before, in parallel. The observation image 101 and the evaluation image 102 are displayed such that even if no change in color occurs in a region where the oxygen saturation is low in the observation image 101, the color changes in the evaluation image 102.

As described above, in the evaluation image, in addition to observation of a wide numerical range of oxygen saturation using the observation image, a subtle difference in oxygen saturation with reference to the oxygen saturation of a specific part to be observed can be highlighted and observed. With the evaluation image, for example, in the abdominal-cavity endoscope system 30, it is possible to discriminate an ischemic region of an organ during a surgical operation. Therefore, for example, the ischemic region can be a basis for judgment of an anastomosis area or an excision area where suture failure is less likely to occur. Furthermore, the lumen endoscope system 20 makes it easy to, for example, visually recognize a subtle difference in the oxygen saturation of a lesion site relative to a normal site or a subtle unevenness in the oxygen saturation of a wide lesion site.

Figure 24:
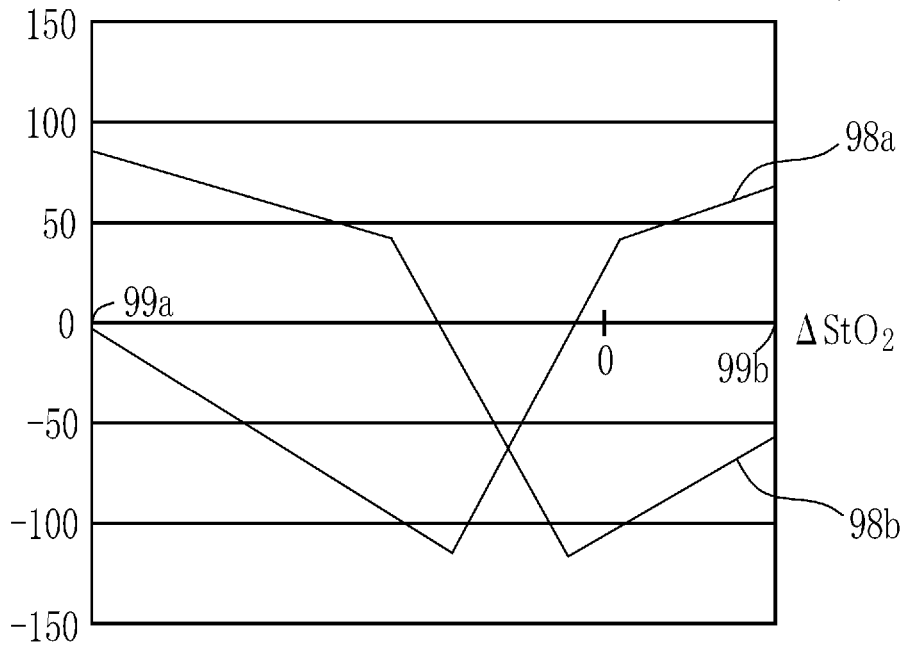
FIG. 24 is an explanatory diagram describing a lower limit value and an upper limit value of an evaluation color table.

Next, creation of the evaluation color table 97 will be described. The evaluation color table 97 may be created as follows. As illustrated in FIG. 24, the color table creation unit 94 may create the evaluation color table 97 such that a lower limit value 99a and an upper limit value 99b of the relative value $\Delta StO_2$ of the first actual measurement value to be associated with the color information of the evaluation image are set in advance. For example, in the evaluation color table 97b, the lower limit value 99a and the upper limit value 99b of the relative value $\Delta StO_2$ of the first actual measurement value are set to −30% and +10%, respectively. In the evaluation color table 97b, the lower limit value 99a and the upper limit value 99b are fixed values. However, when it is desired to visually recognize a smaller difference in oxygen saturation in accordance with the part to be observed, the values in the range of the lower limit value 99a and the upper limit value 99b may be set to narrower values to change fixed values. As a result, it is possible to create an evaluation image in which a smaller difference in oxygen saturation can be visually recognized. Alternatively, the values in the range of the lower limit value 99a and the upper limit value 99b may be set to wider values to change fixed values. As a result, for example, in a case where a region to be observed is a region having a large difference in oxygen saturation and a region having the same color tone is large in the evaluation image, it is possible to obtain an evaluation image in which the color tone is adjusted.

Figure 25:
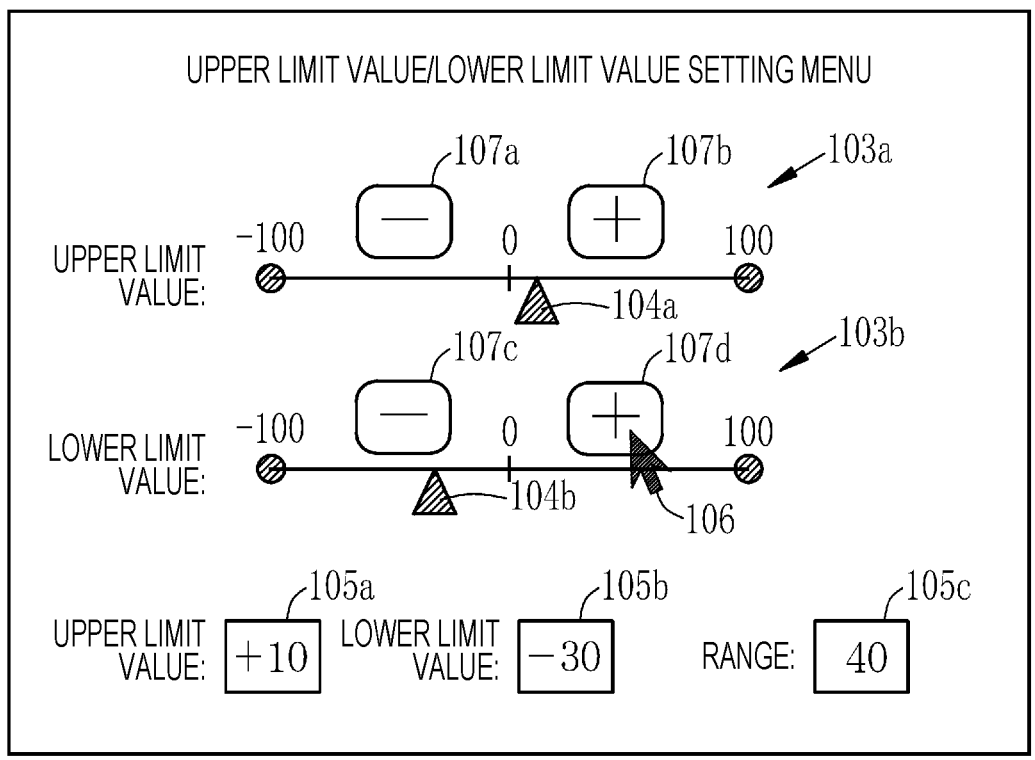
FIG. 25 is an explanatory diagram illustrating an upper limit value/lower limit value setting menu.

The setting acceptance unit 95 may accept an instruction to set the lower limit value 99a and/or the upper limit value 99b of the evaluation color table 97b. The setting instruction is given by the operator. Upon acceptance of an operation of setting the lower limit value 99a of the relative value $\Delta StO_2$ of the first actual measurement value and/or the upper limit value 99b of the relative value $\Delta StO_2$ of the first actual measurement value in response to an operation of the input device 14 or the like, the setting acceptance unit 95 displays an upper limit value/lower limit value setting menu as illustrated in FIG. 25 on the monitor. The upper limit value 99b can be changed in the range of, for example, −100% to +100%. The upper limit value 99b is assigned on a slide bar 103a.

To change the upper limit value 99b, a cursor 106 is operated using the mouse or the like or the foot switch 36 is operated to click a minus button 107a or a plus button 107b. Each time the minus button 107a or the plus button 107b is clicked once with the cursor 106, the value changes by 10%. In a case where the monitor is a touch panel, the operation may be performed by directly pressing the minus button 107a or the plus button 107b on the monitor. To change the lower limit value 99a, as in the case of the upper limit value 99b, a minus button 107c or a plus button 107d is clicked. Each time the minus button 107c or the plus button 107d is clicked once with the cursor 106, the value changes by 10%.

The current setting of the upper limit value 99b is displayed on the slide bar 103a of the upper limit value 99b by a slider 104a. Also for the lower limit value 99a, the current setting of the lower limit value 99a is displayed on a slide bar 103b of the lower limit value 99a by a slider 104b. To largely change the upper limit value 99b and/or the lower limit value 99a, the slider 104a or the slider 104b may be directly moved to change the setting. Further, an upper limit value display portion 105a displays a numerical value indicating the current upper limit value 99b of the relative value $\Delta StO_2$ of the first actual measurement value. Likewise, a lower limit value display portion 105b displays a numerical value indicating the current lower limit value 99a of the relative value $\Delta StO_2$ of the first actual measurement value. Further, a range display portion 105c displays a numerical value indicating the current range between the lower limit value 99a and the upper limit value 99b. The lower limit value 99a and/or the upper limit value 99b set in the way described above are set as the lower limit value 99a and/or the upper limit value 99b of the relative value $\Delta StO_2$ of the first actual measurement value, which are represented by the horizontal axis of the evaluation color table 97b.

When the lower limit value 99a and/or the upper limit value 99b are changed, the graph of the color difference signal Cr 98a and the color difference signal Cb 98b remains unchanged. Thus, even if the value of the upper limit value 99b and/or the value of the lower limit value 99a of the relative value $\Delta StO_2$ of the first actual measurement value are changed, a pseudo-color evaluation image is displayed such that, in the evaluation image, the lower limit value 99a of the relative value $\Delta StO_2$ of the first actual measurement value corresponds to blue, the color approaches red as the relative value $\Delta StO_2$ of the first actual measurement value increases, and the upper limit value 99b of the relative value $\Delta StO_2$ of the first actual measurement value corresponds to red.

The color table creation unit 94 creates the evaluation color table 97b such that, even if the lower limit value 99a and/or the upper limit value 99b of the relative value $\Delta StO_2$ of the first actual measurement value are changed, the relative value $\Delta StO_2$ of the first actual measurement value in a case where it is 0 (zero) and yellow in the evaluation image are associated with each other. Accordingly, in a case where the oxygen saturation is the first reference value, the color tone remains fixed to yellow. Even if the oxygen saturation of the tissue to be observed changes, a difference in the oxygen saturation of the tissue to be observed can be visually recognized using a similar reference.

Further, the color table creation unit 94 may calculate the lower limit value 99a of the relative value $\Delta StO_2$ of the first actual measurement value on the basis of the second reference value different from the first reference value. In this case, the lower limit value 99a of the relative value $\Delta StO_2$ of the first actual measurement value is set to the relative value of the second reference value relative to the first reference value. The second reference value is calculated, for example, on the basis of third spectral images obtained by capturing an image of a third observation target, which is a region including the ischemic site, as a photographic subject. The image signals for the second reference value (see FIG. 9), the calculation method, and the like are similar to those of the first reference value. Thus, the second reference value is an average value of oxygen saturation in the region including the ischemic site.

The second reference value is acquired in accordance with an instruction from the operator in a way similar to that of the first reference value. For example, the timing at which the operator presses the scope button, which is the reference value calculation instruction portion 28b, is made different from the timing at which the first reference value is acquired. As a result, the calculation of the first reference value and the calculation of the second reference value can be performed in accordance with an instruction from the reference value calculation instruction portion 28b. Specifically, the operator observes a region for which the first reference value is desired to be set, such as the normal site, acquires second spectral images using, as a first part to be observed, a region for which the scope button, which is the reference value calculation instruction portion 28b, is pressed once for the first time, and calculates the first reference value. Then, the operator observes a region for which the second reference value is desired to be set, such as the ischemic site, and presses the scope button, which is the reference value calculation instruction portion 28b. The operator acquires third spectral images using, as a second part to be observed, a region for which the scope button is pressed for the second time, and calculates a third actual measurement value and a second reference value.

Specifically, a third actual measurement value is calculated by the actual measurement value calculation unit 83 in a way similar to that of a first actual measurement value and a second actual measurement value. The reference value calculation unit 84 averages third actual measurement values of oxygen saturation at the respective pixel locations, which are calculated by the actual measurement value calculation unit 83, in, for example, the range of one spectral image or the like. The calculated averaged value is set as a second reference value of oxygen saturation.

The relative value calculation unit 75 calculates a relative value of the second reference value with reference to the first reference value. If the second reference value is represented by $StO_2(STD2)$ and the relative value of the second reference value $StO_2(STD2)$ is represented by $\Delta StO_2(LL)$, the relative value $\Delta StO_2(LL)$ of the second reference value $StO_2(STD2)$ is a value obtained by subtracting the second reference value $StO_2(STD2)$ from the first reference value $StO_2(STD)$. When the relative value $\Delta StO_2(LL)$ of the second reference value $StO_2(STD2)$ is expressed by an equation, the following Equation (2) is obtained. The relative value is a relative value calculated with reference to the first reference value and thus has the same unit (%) as that of the oxygen saturation.

$$StO_2(STD) - StO_2(STD2) = \Delta StO_2(LL) \qquad (2)$$

Figure 26:
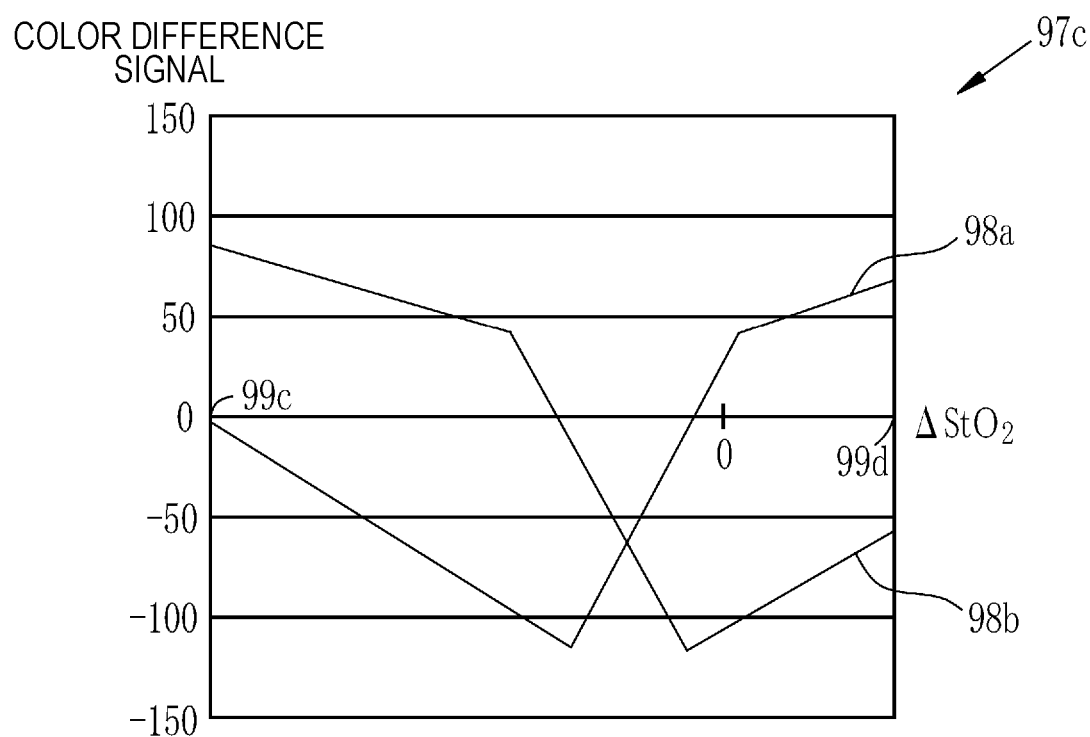
FIG. 26 is an explanatory diagram describing setting of a lower limit value of an evaluation color table.

As illustrated in FIG. 26, as described above, the relative value $\Delta StO_2(LL)$ of the second reference value $StO_2(STD2)$ calculated in the way described above is set as a lower limit value 99c of the relative value $\Delta StO_2$ of the first actual measurement value in the evaluation color table 97c. Accordingly, in response to a simple instruction given by the operator pressing the scope button, an evaluation image based on the appropriate evaluation color table 97 in which two references, namely, the ischemic site and the normal site of the tissue to be observed, are set, can be displayed. Thus, a site where the blood flow is larger than that of the ischemic site, such as a normal portion, can be easily and more clearly visually recognized. An upper limit value 99d of the evaluation color table 97c may also be set using a reference value in a similar manner.

Figure 27:
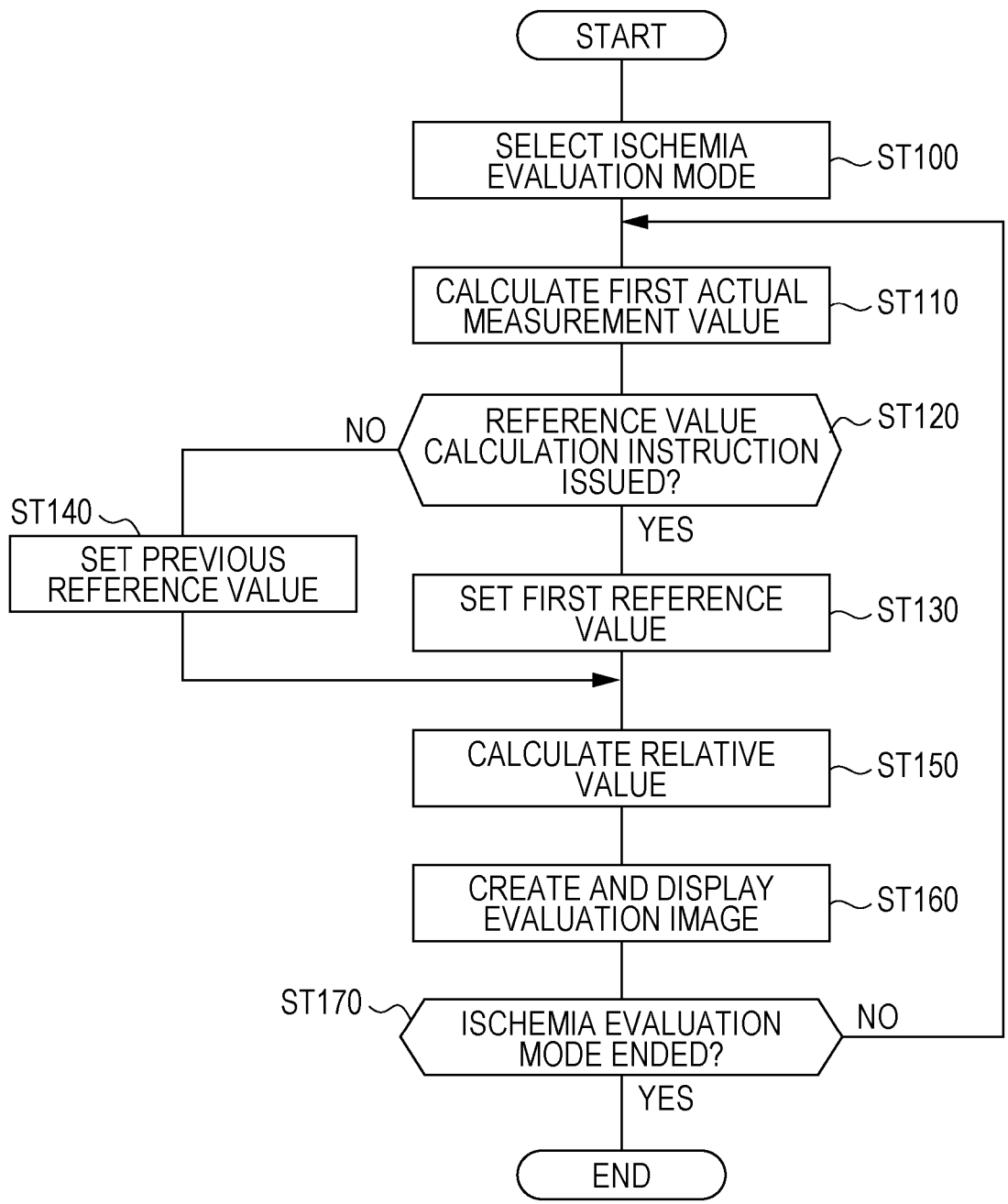
FIG. 27 is a flow diagram illustrating the flow in the ischemia evaluation mode.

Next, the operation of the present invention will be described with reference to a flowchart in FIG. 27 and an observation image and an evaluation image in FIG. 28. For example, when performing the surgical excision of the large intestine using the lumen endoscope system 20 and the abdominal-cavity endoscope system 30, the operator uses the lumen endoscope apparatus 22, which is set to the normal observation mode, to search for the site where the tumor portion has occurred in the large intestine. Then, the operator inserts a clip device into the tumor portion through the forceps channel, and operates the clip device to compress a relatively thick blood vessel near the tumor portion with the clip. The tissue around the blood vessel compressed with the clip falls into an ischemic state, and a hypoxic region in which the oxygen saturation of the tissue being observed is reduced is obtained. The hypoxic region serves as a mark for specifying the position of the tumor portion in the next surgery. After placing the mark with the clip, the operator removes the lumen endoscope apparatus 22 from the large intestine.

In the next surgery, the abdominal-cavity endoscope apparatus 32 is inserted into the abdomen of the patient. The area marked using the clip is observed with the lumen endoscope apparatus 22 in the oxygen saturation mode of the abdominal-cavity endoscope apparatus 32. The observation image 101 is created using the observation color table 96. The observation image 101 is displayed on the monitor, and, for example, a portion in which the oxygen saturation is reduced can be confirmed as the tumor portion using the clip. Then, to determine an excision area or an anastomosis area, the same region as the region for which the observation image 101 is acquired is observed in the ischemia evaluation mode (step ST100). Here, a first actual measurement value is calculated (step ST110). To acquire a first reference value, a region for which the reference value is desired to be set is observed, and the scope button, which is the reference value calculation instruction portion 28*b*, is pressed (YES in step ST120). Here, the operator observes the same region as that observed in the oxygen saturation mode and issues a reference value calculation instruction. The reference value calculation instruction is issued, the mode is switched to the reference-value calculation mode, and a first reference value is calculated (step ST130). When the first reference value is calculated, the mode returns to the ischemia evaluation mode. If the previously used reference value is used again (NO in step ST120), the previous reference value is set as the first reference value (step ST140).

In the ischemia evaluation mode, the relative value $\Delta StO_2$ of the first actual measurement value, which is the relative value of the oxygen saturation of the tissue to be observed, is calculated (step ST150), and the evaluation image 102 is created using the evaluation color table 97. The evaluation image 102 is displayed on the monitor (step ST160), and a more detailed difference in oxygen saturation than the observation image 101 is visually recognized. The operator specifies the position of the tumor portion and checks the oxygen saturation, the ischemic state, and the like around the tumor portion. To create the evaluation image 102 again, the process returns to the actual measurement value calculation (NO in step ST170). When the creation of the evaluation image 102 is ended, the ischemia evaluation mode is ended (YES in step ST170). For example, an excision area or an anastomosis area can be determined by selecting an area where the blood flow is as large as possible from the evaluation image 102. In addition, even if a portion where the oxygen saturation is low exists, an excision area or an anastomosis area where suture failure is less likely to occur can be determined by selecting the boundary between an ischemic region and a normal region, avoiding the ischemic region, avoiding an area having a mixture of congestion and ischemia, selecting a homogeneous area, or the like. After the treatment is completed, the abdominal-cavity endoscope apparatus 32 is removed from the patient, and a procedure for completing the surgery is performed.

In the embodiment described above, the hardware structure of processing units that execute various types of processes, such as the central control unit 56*a*, the image acquisition unit 57, the image processing unit 58, and the display control unit 59, is that of various types of processors presented below. The various types of processors include a CPU (Central Processing Unit), which is a general-purpose processor executing software (program) to function as various types of processing units, a programmable logic device (PLD) such as an FPGA (Field Programmable Gate Array), which is a processor whose circuit configuration is changeable after manufacture, a dedicated electric circuit (Graphical Processing Unit: GPU), which is a processor having a circuit configuration specifically designed to cause various types of processes to be executed, and so on.

A single processing unit may be configured as one of the various types of processors or as a combination of two or more processors of the same type or different types (for example, a plurality of FPGAs, a combination of a CPU and an FPGA, or a combination of a GPU and a CPU). Alternatively, a plurality of processing units may be configured as a single processor. Examples of the configuration of a plurality of processing units as a single processor include, first, a form in which, as typified by a computer such as a client or a server, the single processor is configured as a combination of one or more CPUs and software and the processor functions as the plurality of processing units. The examples include, second, a form in which, as typified by a system on chip (SoC) or the like, a processor is used in which the functions of the entire system including the plurality of processing units are implemented as one IC (Integrated Circuit) chip. As described above, the various types of processing units are configured by using one or more of the various types of processors described above as a hardware structure.

Furthermore, the hardware structure of these various types of processors is, more specifically, an electric circuit (circuitry) including a combination of circuit elements such as semiconductor elements.

REFERENCE SIGNS LIST

10 endoscope system
12 display device
14 input device
20 lumen endoscope system
21 lumen light source device
22 lumen endoscope apparatus
23 lumen processor apparatus
24*a* lumen endoscope operation portion
24*b* lumen endoscope insertion portion
25 scope distal end portion
26 forceps channel
26*a* forceps inlet
26*b* forceps outlet
27 bending portion
28*a* mode switch
28*b* reference value calculation instruction portion
29 angle knob
30 abdominal-cavity endoscope system
31 abdominal-cavity light source device
32 abdominal-cavity endoscope apparatus
33 abdominal-cavity processor apparatus
34 abdominal-cavity endoscope insertion portion
35 abdominal-cavity endoscope distal end portion
36 foot switch
37 pneumoperitoneum device
38 treatment tool
39*a*, 39*b* trocar
41 light source
41*a* BS-LED
41*b* BL-LED
41*c* G-LED
41*d* R-LED
42 light source control unit
43 light guide
44*a* illumination optical system
44*b* imaging optical system
45 illumination lens
46 objective lens
48 imaging sensor
49 imaging surface
51 pixel
52 B color filter
53 G color filter
54 R color filter
55 imaging control unit
56 control unit
56*a* central control unit
57 image acquisition unit
58 image processing unit
59 display control unit
59*a* display image selection unit
61 DSP
62 noise reduction unit
63 conversion unit 71 normal image processing unit
72 special image processing unit
73 measurement value calculation unit
74 reference value calculation instruction acceptance unit
75 relative value calculation unit
76 image generation unit
81 signal ratio calculation unit
82 correlation storage unit
83 actual measurement value calculation unit
84 reference value calculation unit
86 two-dimensional table
91 graph
91a light absorption coefficient of oxyhemoglobin
91b light absorption coefficient of deoxyhemoglobin
92a lower-limit line
92b upper-limit line
93 color table storage unit
94 color table creation unit
95 setting acceptance unit
96 observation color table
97a, 97b, 97c evaluation color table
98a color difference signal Cr
98b color difference signal Cb
99a, 99c lower limit value
99b, 99d upper limit value
100a, 100b color bar
101 observation image
102 evaluation image
103a, 103b slide bar
104a, 104b slider
105a upper limit value display portion
105b lower limit value display portion
105c range display portion
106 cursor
107a, 107c minus button
107b, 107d plus button
X row direction
Y column direction
ST100 to ST170 step

What is claimed is:

1. An endoscope system comprising:
a processor that calculates a first actual measurement value of oxygen saturation of a tissue to be observed on the basis of a plurality of first spectral images,
calculates a first reference value of the oxygen saturation of the tissue to be observed on the basis of a plurality of second spectral images,
calculates a relative value of the first actual measurement value with reference to the first reference value, and
generates an image of the relative value of the first actual measurement value on the basis of an evaluation color table to generate an evaluation oxygen-saturation image; and
a display that displays at least the evaluation oxygen-saturation image,
wherein the processor generates an image of the first actual measurement value on the basis of an observation color table to generate an observation oxygen-saturation image, and
switches between an oxygen saturation mode for displaying at least the observation oxygen-saturation image on the display and an ischemia evaluation mode for displaying at least the evaluation oxygen-saturation image on the display.

2. The endoscope system according to claim 1, wherein the processor sets, as the relative value of the first actual measurement value, a value obtained by subtracting the first reference value from the first actual measurement value.

3. The endoscope system according to claim 1, wherein the processor generates the observation oxygen-saturation image on the basis of the observation color table in which a value in a range from 0% to 100% of the oxygen saturation and color information of the observation oxygen-saturation image are associated with each other in advance.

4. The endoscope system according to claim 1, wherein the processor creates the evaluation color table in which the relative value of the first actual measurement value and color information of the evaluation oxygen-saturation image are associated with each other.

5. The endoscope system according to claim 1, wherein in the evaluation color table, the relative value of the first actual measurement value in a case where the relative value is 0 and a specific color in a warm color system of the evaluation oxygen-saturation image are associated with each other.

6. The endoscope system according to claim 4, wherein the processor sets a lower limit value and/or an upper limit value of the relative value of the first actual measurement value associated with color information of the evaluation oxygen-saturation image to create the evaluation color table.

7. The endoscope system according to claim 6, wherein the processor accepts an instruction to set the lower limit value and/or the upper limit value, and
creates the evaluation color table using the lower limit value and/or the upper limit value based on the instruction.

8. The endoscope system according to claim 6, wherein the processor calculates a second reference value of the oxygen saturation of the tissue to be observed on the basis of a plurality of third spectral images,
calculates a relative value of the second reference value with reference to the first reference value, and
sets the relative value of the second reference value as the lower limit value.

9. The endoscope system according to claim 1, wherein the processor accepts an instruction to calculate the first reference value, and
calculates the first reference value in accordance with the instruction.

10. The endoscope system according to claim 8, wherein the processor calculates the first reference value or the second reference value by averaging second actual measurement values or third actual measurement values of the oxygen saturation, each of the second actual measurement values being calculated for a corresponding one of pixels of the plurality of second spectral images, each of the third actual measurement values being calculated for a corresponding one of pixels of the plurality of third spectral images.

11. The endoscope system according to claim 1, wherein the processor determines a signal ratio having dependence on both the oxygen saturation and blood volume on the basis of the plurality of first spectral images, the plurality of second spectral images, or a plurality of third spectral images,
stores a correlation between the oxygen saturation and the signal ratio, and
calculates the first actual measurement value, a second actual measurement value, or a third actual measurement value of the oxygen saturation corresponding to the signal ratio on the basis of the correlation.

12. The endoscope system according to claim 8, wherein the first spectral images are images obtained by capturing an image of a first observation target that includes a lesion, and the second spectral images or the third spectral images are images obtained by capturing an image of a second observation target or a third observation target that does not include the lesion.

13. A method for activating an endoscope system, comprising:

an actual measurement value calculation step of calculating a first actual measurement value of oxygen saturation of a tissue to be observed on the basis of a plurality of first spectral images;

a reference value calculation step of calculating a first reference value of the oxygen saturation of the tissue to be observed on the basis of a plurality of second spectral images;

a relative value calculation step of calculating a relative value of the first actual measurement value with reference to the first reference value;

an evaluation image generation step of generating an image of the relative value of the first actual measurement value on the basis of an evaluation color table to generate an evaluation oxygen-saturation image; and a display step of displaying the evaluation oxygen-saturation image, wherein the method for activating an endoscope system further comprises an observation image generation step of generating an image of the first actual measurement value on the basis of an observation color table to generate an observation oxygen-saturation image, and an oxygen saturation mode for displaying at least the observation oxygen-saturation image on the display and an ischemia evaluation mode for displaying at least the evaluation oxygen-saturation image on the display are switched in the display step.

14. An image processing apparatus that an endoscope system comprises, wherein the image processing apparatus calculates a first actual measurement value of oxygen saturation of a tissue to be observed on the basis of a plurality of first spectral images, calculates a first reference value of the oxygen saturation of the tissue to be observed on the basis of a plurality of second spectral images, calculates a relative value of the first actual measurement value with reference to the first reference value, and generates an image of the relative value of the first actual measurement value on the basis of an evaluation color table to generate an evaluation oxygen-saturation image, wherein the image processing apparatus generates an image of the first actual measurement value on the basis of an observation color table to generate an observation oxygen-saturation image, and switches between an oxygen saturation mode for displaying at least the observation oxygen-saturation image on the display and an ischemia evaluation mode for displaying at least the evaluation oxygen-saturation image on the display.

* * * * *